US012806304B2

(12) United States Patent
Boyd et al.

(10) Patent No.: US 12,806,304 B2
(45) Date of Patent: Nov. 24, 2026

(54) SYSTEM AND METHOD FOR HIGH EFFICIENCY FILTERING AND REMOVAL OF AIRBORNE PATHOGENS FROM A VOLUME OF GAS

(71) Applicant: FACE INTERNATIONAL CORPORATION, Norfolk, VA (US)

(72) Inventors: Clark D. Boyd, Hampton, VA (US); Bradbury R. Face, Smithfield, VA (US)

(73) Assignee: FACE INTERNATIONAL CORPORATION, Norfolk, VA (US)

( * ) Notice: Subject to any disclaimer, the term of this patent is extended or adjusted under 35 U.S.C. 154(b) by 314 days.

(21) Appl. No.: 18/279,184

(22) PCT Filed: Feb. 28, 2022

(86) PCT No.: PCT/US2022/018229
§ 371 (c)(1),
(2) Date: Aug. 28, 2023

(87) PCT Pub. No.: WO2022/183134
PCT Pub. Date: Sep. 1, 2022

(65) Prior Publication Data
US 2024/0139369 A1 May 2, 2024

Related U.S. Application Data

(60) Provisional application No. 63/154,787, filed on Feb. 28, 2021.

(51) Int. Cl.
*A61L 9/20* (2006.01)
*A61L 9/22* (2006.01)
(Continued)

(52) U.S. Cl.
CPC .................. *A61L 9/20* (2013.01); *A61L 9/22* (2013.01); *B01D 53/265* (2013.01); *B03C 3/04* (2013.01);
(Continued)

(58) Field of Classification Search
CPC ... F24F 8/30; F24F 3/14; F24F 5/0042; A61L 9/22; B01D 53/265; C02F 1/02
See application file for complete search history.

(56) References Cited

U.S. PATENT DOCUMENTS

2005/0139552 A1* 6/2005 Forsberg .................. E03B 3/28 62/635
2006/0257299 A1* 11/2006 Lanz ......................... B03C 3/08 422/186.04
(Continued)

FOREIGN PATENT DOCUMENTS

WO WO-2020229791 A1 * 11/2020 ............. B01D 5/006

*Primary Examiner* — Sean E Conley
(74) *Attorney, Agent, or Firm* — Lowndes; Stephen C. Thomas

(57) ABSTRACT

A system and method for removing unwanted particles and pathogens, including but not limited to viruses, from a volume of gas. The system exhibits low resistance to air flow, allowing a high volume flow and rate of gas volume to be processed. Cold surfaces reduce the temperature of incoming gas causing condensation of water from the gas. The condensate contains unwanted particles and pathogens that have been removed from the volume of gas. The condensate is caused to pass over heated surfaces that comprising a hydrophobic coating, and also comprising catalytic surfaces with anti-viral coatings to neutralize contagions. Micro-spray nozzles, which may incorporate ionization, may be utilized to spray collected water onto the heated surfaces where the contagion may be utilized. The system may comprise multiple stages. The system provides better contagion neutralization and higher flow rates than
(Continued)

prior art systems while using less energy, and producing less noise.

21 Claims, 15 Drawing Sheets

(51) Int. Cl.

| | |
|---|---|
| ***B01D 53/26*** | (2006.01) |
| ***B03C 3/04*** | (2006.01) |
| ***C02F 1/02*** | (2023.01) |
| ***C02F 1/72*** | (2023.01) |
| ***F24F 3/14*** | (2006.01) |
| ***F24F 5/00*** | (2006.01) |
| ***F24F 8/30*** | (2021.01) |
| *F24F 13/22* | (2006.01) |

(52) U.S. Cl.

CPC ................ *C02F 1/02* (2013.01); *C02F 1/725* (2013.01); *F24F 3/14* (2013.01); *F24F 5/0042* (2013.01); *F24F 8/30* (2021.01); *A61L 2209/111* (2013.01); *A61L 2209/12* (2013.01); *A61L 2209/22* (2013.01); *B01D 2257/80* (2013.01); *B01D 2258/06* (2013.01); *C02F 2303/04* (2013.01); *F24F 2013/228* (2013.01)

(56) References Cited

U.S. PATENT DOCUMENTS

| | | | | |
|---|---|---|---|---|
| 2007/0221582 | A1* | 9/2007 | Holland ................. | B01D 53/90<br>210/748.11 |
| 2008/0314062 | A1* | 12/2008 | Ritchey ................... | F28B 11/00<br>62/119 |
| 2013/0255280 | A1* | 10/2013 | Murphy ............... | B01D 5/0042<br>62/3.4 |
| 2017/0254053 | A1* | 9/2017 | Kumar ...................... | E03B 3/28 |
| 2018/0356116 | A1* | 12/2018 | Winders .................. | F24F 13/22 |

* cited by examiner (INLET STAGE)

(OUTLET STAGE)

(1ST STAGE OF INTERMEDIATE STAGE PAIR)

(2ND STAGE OF INTERMEDIATE STAGE PAIR)

(INLET STAGE)

(1ST INTERMEDIATE STAGE)

(2ND INTERMEDIATE STAGE)

(OUTLET STAGE)

SYSTEM AND METHOD FOR HIGH EFFICIENCY FILTERING AND REMOVAL OF AIRBORNE PATHOGENS FROM A VOLUME OF GAS

REFERENCE

This non-provisional patent application claims benefit of priority to U.S. Provisional Patent Application Ser. No. 63/154,787, entitled MULTIFACETED SYSTEM FOR HIGH EFFICIENCY FILTERING AND DESTRUCTION OF AIRBORNE PATHOGENS, filed in the United States Patent and Trademark Office (USPTO) on Feb. 28, 2021, the disclosure of which is incorporated herein by reference in its entirety.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISK

Not applicable.

BACKGROUND OF THE INVENTION

1. Field of the Invention

The field of the invention relates generally to systems and methods for filtration and removal of airborne particulates, contagions and other unwanted substances.

2. Background Art

It is well known that airborne pathogens can cause contagion, and that airborne particles can have serious health effects, in both human and non-human populations. The spread of airborne pathogens and other biohazard materials, for example, can cause a pandemic or epidemic that can rapidly spread through populations, causing severe health problems or death in such populations, and resulting in severe and long-lasting economic damage and even threats to national security. An example of this is the spread of variants of the coronavirus that causes Covid-19 disease, which began circulation in the global human population in 2019 and has continued into 2022.

The spread of unwanted particles can likewise cause increased rates of health problems in populations, with the same negative results. As an example, the spread of airborne carcinogenic matter can cause increased cancer rates in populations causing severe health problems in individuals resulting long-lasing economic damage.

Indoor environments and other enclosed spaces represent a heightened risk of disease or other negative health effects due airborne unwanted particles or pathogens, as air in such spaces is typically recirculated through heating, ventilation and air conditioning ("HVAC") and other systems. In these enclosed environments, air may be recirculated without any method for allowing the unwanted particles or pathogens to escape into the environment or atmosphere outside the enclosed space where it can be carried away by external winds. Thus, when unwanted particles or pathogens are introduced into such enclosed spaces, they can linger in airborne fashion for hours, days or even longer, creating increased health risks for individuals occupying the enclosed space.

In some situations, it may be possible to vent the space in order to replace the contaminated internal air with uncontaminated external air. However, in many situations, such venting is not possible. For example, in large buildings in which there are numerous interior enclosed spaces it is generally not feasible to vent the interior spaces. Further, in most enclosed spaces in which individuals congregate, there is a need to control the temperature of the air through air conditioning or heating. Thus, venting is not a viable in a majority of applications.

Traditional particulate filtering of unwanted particles or pathogens is also problematic. Virus pathogens, for example, can be of very small dimension and therefore very difficult to filter from a volume of use by simply using a particulate filter. As an example, a SARS-CoV-2 virion, the virus that causes coronavirus disease 2019 (also known as human coronavirus 2019, HCoV-19 or hCoV-190, the respiratory illness responsible for the COVID-19 pandemic) is on the order of 50-20 nanometers in diameter. High Efficiency Particulate Air (HEPA) filters have been proposed for use in removing the SARS-CoV-2 virion from volumes of air. However, the use of particulate filters such as HEPA filters that are fine enough to remove a virus from a gas such as air has significant drawbacks. HEPA filters, being physical blocking filters, create a severe resistance to air flow and thus require large blowers to push the air through the filter. These blowers are extremely noisy and consume large amounts of electrical energy. The noise factor alone may render such systems unusable for most indoor enclosed spaces. Further the size of the SARS-CoV-2 virion is at the very low end of the range of HEPA filters, meaning that multiple stages of HEPA filtering may be required in order to remove a pathogen such as the SARS-CoV-2 virion from a volume of air. This exacerbates the known problems of HEPA filter (high noise levels, large energy consumption). A further drawback of HEPA filters is that, due to the very small openings required in order to filter, for example, the small SARS-CoV-2 virion, the filters must be changed frequently, resulting in used filter elements containing a large amount of active virus, which is a biohazard that must be handled in accordance with regulatory requirements at great expense and inconvenience to the user. Disposing of such biohazard used filter creates an additional and inordinate cost to the use of HEPA filters.

What is needed in the art, therefore, is an apparatus and/or method adapted to remove unwanted particles and pathogens from a volume of air that is energy efficient, does not exhibit loud noise so as to cause distraction, can be readily manufactured at a low cost, can operate independently of other systems, does not result in biohazard waste, and is easily deployable in a wide variety of large and small enclosed spaces.

BRIEF SUMMARY OF THE INVENTION

The present invention comprises a method and system, or device, that have one or more of the following features and/or steps, which alone or in any combination may comprise patentable subject matter. The present invention overcomes the aforementioned drawbacks of the prior art as described below.

The present method and system of the invention remove unwanted particles and pathogens from a volume of air, in embodiments on a continuing basis, so as to reduce the threat of the spread of disease or other harmful effects of such airborne unwanted particles and pathogens on populations of individuals, both human and non-human. The present method and system of the invention are especially useful in pandemic situations in which airborne virus or other biohazards are characterized by airborne transmission. In such cases, the present method and system of the invention is operative to dramatically reduce the rate of airborne transmission of a pathogen, for example viruses, bacteria or other biological material that may cause disease, by removing the subject pathogen (for example, a given virus) from a volume of air so that, for example and not by way of limitation, enclosed environments such as the interiors of buildings, which may contain dangerous levels of airborne pathogens, can be rendered safe for use by individuals without fear of a particular pathogen, and a resulting disease, being transmitted by airborne transmission. Such enclosed environments may be, for example, rooms of hospitals, doctors offices, surgery centers, and other medical facilities; classrooms; government buildings; public buildings; museums and other buildings that are frequented by the public; the interior of transportation modalities such as airplanes, trains, busses, ships, cars, and the like; sports facilities; homes; hotels; and virtually any enclosed environment in which human or non-human individuals are likely to congregate. These are non-limiting examples of some applications of the inventive system and method.

The system and method of the invention, in embodiments, is operable to remove unwanted materials from a volume of gas, such as air. Such unwanted materials may include dust, pollen, mold, bacteria, viruses, and any other type of airborne particles, without using substrate or other types of mechanical filter material.

The present method and system of the invention overcome the shortcomings of the prior art by removing unwanted material such as particles and pathogens from a volume of air without the use of mechanical filtration such as, for example, High Efficiency Particulate Air (HEPA) or Ultra Low Particulate Air (ULPA) filters. The system of the invention does not utilize large, noisy air blowers such as those used to establish negative pressure rooms or facilities. Advantages of the method and system of the invention are characterized by 1) very low-pressure drop through the system, allowing high volume of air flow, since the system of the invention does not rely on physical blockage of particulates or pathogens; 2) no dirty or toxic air filters to clean or destroy; 3) much lower noise; and 4) less electric energy power consumption requirements, than HEPA, ULPA or negative pressure systems which must work against a higher head pressure to move a given volume of air. The method and system of the invention is characterized by a pressure drop that is less than the pressure drop of systems of the prior art as a result of the open-air flow design of the system.

In embodiments, the method and system of the device operate, generally, by motivating a volume of gas (which may be air), which may be a continuing volume, typically but not necessarily through an enclosure, in which the elements of the system are disposed. The incoming volume of gas, which is characterized by an inlet gas or air temperature, is motivated in proximity to, or in contact with, a first surface having a first temperature such that the inlet air comes into thermal communication with the first surface. In embodiments, the volume of air may then continues to be motivated such that is comes into proximity to, or in contact with, a second surface having a second temperature, such that the air comes into thermal communication with the second surface. The volume of gas may continue to be motivated such that it comes into thermal communication with a third surface having a third temperature, and, in embodiments, the volume of air may continue to be motivated such that it comes into thermal communication with a fourth surface having a fourth temperature, and so on, for any number of surfaces, each surface characterized by its own temperature. Some of the surfaces may be characterized by the same temperature. The temperatures of the individual surfaces may be any combination of temperatures that causes water in the gas to condense, forming a volume of condensate, the condensate being motivated away from the surfaces, carrying with it unwanted matter which may include pathogens that are desired to be removed from the volume of gas. The condensate is then motivated into one or more collection reservoirs where it may be treated to neutralize pathogens that have been removed from the gas and carried into the reservoir(s) by the collection of the condensate into the reservoir(s).

In embodiments, temperatures of the surfaces may be higher or lower than the incoming volume of gas, as long as the surfaces are characterized by temperatures that cause water to condense as the volume of air is motivated through the enclosure.

In embodiments, the incoming inlet gas may be cooled by causing it to impinge (i.e. come into thermal communication with) one or more surfaces that are characterized by a temperature that is colder than the gas impinging the surfaces, causing water ($H_2O$) in the volume of gas to condense and precipitate, causing the gas to become cooled air, forming a volume of condensate containing unwanted materials, which may include pathogens. The condensate is then motivated to a collection reservoir where it may be treated to remove the unwanted particles or to neutralize the pathogens. The gas may then be heated by causing the gas to come into come into thermal communication with surfaces that are at a higher temperature than the cooled gas, creating a heated volume of gas that is able to reabsorb water. The heated volume of gas may then be subjected to cooling again by causing the heated volume of gas to impinge on (i.e. come into thermal communication with) a further cold surface, cooling the heated volume of gas, and causing further water in the volume of gas to condense and precipitate, resulting in a further condensate containing unwanted particles and pathogens. The further condensate may be collected in the same, or a different, reservoir, and treated to remove the unwanted particles or to neutralize the pathogens, or both. This cooling-condensation-precipitation-collecting-treating cycle may be repeated for a plurality of stages or cycles, each successive stage or cycle resulting in successively cleaner volumes of gas that contain fewer unwanted materials or pathogens with each successive stage.

Ultraviolet lighting or other detection means may be used to ascertain the remaining level of unwanted particles and pathogens in each successive stage, or cycle, in order to determine whether the air meets a standard to be considered safe for its intended use. Ultraviolet lighting may be used at any stage in order to further neutralize pathogens in the volume of air as it is motivated into, through, and out of the system of the invention (e.g., through the enclosure).

In embodiments, the system of the invention may comprise any number of fans, enclosures, blowers, baffles, structures, openings, housings, gas directing surfaces, shapes of enclosures or components or other features so as to effectuate and direct the movement and motivation of the volume of gas 002 into, through, and out of enclosure 100 such that the volume of gas 002 impinges the cold surfaces and hot surfaces of the thermoelectric modules 104 as taught herein such that unwanted particles and pathogens are removed from the volume of air 002 via condensation as it passes through the system.

In embodiments, a plurality of complete stages of thermoelectric module pairs, in any number and in any combination, may be employed to increase removal rate of unwanted particles or pathogens, or both, in order to achieve goals with scalable power consumption. Each additional complete thermoelectric module pair stage can feed directly into the next complete stage. It is not necessary that each of the complete stages in such a multi-stage system each comprise the same type or number of sub-stages.

In embodiments the inlet filter is characterized as requiring little power for passing air 002, since may be, for example, a relatively coarse impingement filter. No HEPA type mechanical filtration is required by the system and method of the invention. Thus, it is an advantage of the system and method of the invention that it requires much less power consumption, cost and maintenance than HEPA and other filters of the prior art.

In embodiments, the invention comprises a system for removing unwanted materials from a continuing volume of gas, comprising: an enclosure comprising a fan for moving a continuing volume of gas through the enclosure, the enclosure having an inlet enabling the continuing volume of gas to enter the enclosure, and a second opening enabling the continuing volume of gas to exit the enclosure, the continuing volume of gas characterized by a temperature; at least one cold surface that is at a lower temperature than the continuing volume of gas, such that water in the air condenses and precipitates from the gas as the gas comes into thermal communication with the at least one cold surface, forming a condensate comprising the unwanted materials; at least one hot surface that is at a higher temperature than the continuing volume of gas, that heats the continuing volume of gas as the gas comes into thermal communication with the at least one hot surface; and at least one collection reservoir in fluid communication with the condensate so that it collects the condensate; wherein the continuing volume of gas is motivated though an outlet opening, wherein the continuing volume of gas that exits the enclosure through the outlet opening has a lower count of unwanted materials to volume of gas than the continuing volume of gas that entered the enclosure.

In embodiments, the temperature of the at least one cold surface may be between 0° C. and 15° C., and the temperature of the at least one hot surface may be between 40° C. and 70° C. In embodiments, the collection reservoir may comprise a catalytic material for neutralizing a pathogen. In embodiments, the system of claim 1, wherein the condensate in the at least one collection reservoir is maintained at a temperature of 56° C. or greater.

In an embodiment, the at least one cold surface may further be defined as a plurality of cold surfaces, the at least one hot surface is defined as a plurality of hot surfaces, the number of cold surfaces, the number of hot surfaces, and the number of collection reservoirs may be the same. The cold surfaces and hot surfaces may be arranged such that the volume of air comes into thermal communication first with a cold surface, and after that, comes into thermal communication with a hot surface, and then comes into thermal communication with alternating cold surfaces and hot surfaces, as the continuing volume of gas passes through the enclosure.

In embodiments, the system may further comprise an ionizer disposed between the inlet and the at least one cold surface, the ionizer operable to ionize the continuing volume of gas and unwanted materials carried by the continuing volume of gas as the continuing volume of gas passes though the ionizer. In embodiments, the system may comprise at least one ultraviolet light source disposed within the enclosure, the at least one ultraviolet light source irradiating at least a portion of the continuing volume of gas such that the portion of continuing volume of gas receives at least 10-20 mJ/cm2 dosage of UV-A, UV-B, or UV-C light energy. The system may further comprise at least one mister in communication with a source of fluid, for increasing the volume of water carried by the continuing volume of gas.

In embodiments, the at least one cold surface comprises a hydrophobic coating. In embodiments, the at least one hot surface comprises a catalytic material for neutralizing pathogens.

In embodiments, the mister may be an ultrasonic nebulizer.

In embodiments, the source of fluid to the mister may be a flash boiler that is in communication with the at least one collection reservoir, such that condensate from said at least one collection reservoir is communicated to the flash boiler, where the condensate is heated such that pathogens in the condensate are neutralized, and wherein the resulting heated condensate is communicated to the mister for increasing the amount of water in the continuing volume of gas.

In embodiments, the system of claim 1, the enclosure may comprise a plurality of stackable stages, including at least one inlet stage and at least one outlet stage, wherein the inlet stage receives a continuing volume of gas, passes the continuing volume of gas in proximity to a plurality of alternating cold and hot surfaces, and exits the continuing volume of gas into a following stage, which may be a first intermediate stage of an intermediate stage pair or an outlet stage. In the case in which the following stage is a first intermediate stage of an intermediate stage pair, the continuing volume of gas passes through the intermediate stage pair, coming into thermal communication with a plurality of alternating cold and hot surfaces, resulting in the formation of condensate when the gas comes into thermal communication with the cold surfaces of the intermediate stage pair. The continuing volume of gas may exit into a following stage, which may be another first intermediate stage of an inter-mediate stage pair, or an outlet stage. In the case in which the following stage is an outlet stage, the continuing volume of gas passes through the outlet stage, coming into thermal communication with a plurality of alternating cold and hot surfaces, resulting in the formation of condensate when the gas comes into thermal communication with the cold surfaces of the outlet stage, and the continuing volume of gas exit the enclosure through an outlet opening in the outlet stage.

In embodiments, the system may comprise an inlet stage, and an outlet stage.

In embodiments, the system may comprise an inlet stage, an intermediate stage pair, and an outlet stage.

In embodiments, the system may comprise an inlet stage, a plurality of intermediate stage pairs, and an outlet stage.

In embodiments, the at least one cold surface may be a cold surface of a thermoelectric module, and wherein the at least one hot surfaces is a hot surface of a thermoelectric module.

In embodiments, the continuing volume of gas may be directed to pass between the cold surfaces of a pair of thermoelectric modules arranged so that their cold surfaces are opposing, forming an open volume between them, through which the gas passes, causing the gas to come into thermal communication with said cold surfaces such that the temperature of said gas is lowered, forming condensate containing unwanted materials that are desired to be removed from the continuing volume of gas.

In embodiments, the temperature of the at least one cold surface may be between 0° C. and 15° C. In embodiments, the temperature of the at least one hot surface may be between 40° C. and 70° C. In embodiments, the condensate in the at least one collection reservoir may be maintained at a temperature of 56° C. or greater.

In embodiments, may comprise at least one ultraviolet light source disposed within the enclosure, the at least one ultraviolet light source irradiating at least a portion of the continuing volume of gas with sufficient intensity to neutralize pathogens in the continuing volume of gas.

In embodiments, at least a portion of the surfaces of the collection reservoir that come into contact with said condensate comprises a catalytic material.

In embodiments, the condensate may be pumped from said collection reservoir and sprayed onto said at least one hot surface. In embodiments, the condensate may be wicked from said collection reservoir by capillary action onto said at least one hot surface.

In embodiments, the thermoelectric module may be defined as plurality of an even number of thermoelectric modules, wherein two thermoelectric modules form a thermoelectric module pair, wherein the thermoelectric modules comprising the thermoelectric module pair are arranged so that their cold surfaces are opposing one another, forming an open volume between them, through which said air passes, causing said air to come into contact with, or pass near, said cold surfaces such that the temperature of said air is reduced, causing condensate to form on said cold surfaces, said condensate containing unwanted particles or pathogens that have been removed from said air.

In embodiments, the system of the invention may comprise a plurality of thermoelectric module pairs and a plurality of collection reservoirs, one collection reservoir for each thermoelectric module pair and each collection reservoir associated with a specific thermoelectric module pair, each of said collection reservoirs disposed so as to collect condensate that is motivated from said cold surfaces of the associated thermoelectric module pair by the force gravity.

In embodiments, the system of the invention may comprise at least one pump in fluid communication with at least one of said collection reservoirs for pumping said condensate from said collection reservoirs, further comprising a spray or microspray nozzle in flow communication with said pump, wherein said pump is configured to pump said condensate from said collection reservoir and sprayed onto said hot surfaces through said spray or said microspray nozzle.

In embodiments, the system of the invention may comprise at least one wicking structure in fluid communication with at least one of said collection reservoirs for wicking said condensate from said collection reservoirs onto said at least one hot surface. The wicking structure is microgrooved copper tubing or sintered copper.

In embodiments, the system of the invention may further comprise at least one controllable fan for motivating said air into, and through said enclosure, such that at least a portion of said air comes into thermal communication with said cold surfaces; a controller operable to control said fan; wherein the controller is in communication with a physical memory comprising non-transitory computer readable and executable instructions for controlling power to the fan and the thermoelectric modules; and wherein said controller is adapted to receive user commands for controlling power to said fan and to said thermoelectric modules through at least one of a human user interface or a remote user in communication with said controller.

In embodiments, the controller may further be adapted to receive sensor information from one or more external sensors, and, and to control the system of the invention into an operational state when one or more sensors detect that an unwanted material is present in the environment outside an enclosure of the system. The controller may also be adapted to receive sensor information from one or more internal sensors, and to communicate said sensor information to a user through said human user interface or to communicate said sensor information to a remote user in communication with said controller.

In embodiments, the invention comprises a method for removing unwanted particles and pathogens from a continuing volume of gas, comprising the steps of motivating the continuing volume of gas through an enclosure; ionizing the continuing volume of gas; adding water droplets, microdroplets or molecules to the continuing volume of gas; cooling the continuing volume of gas such that water in the gas condenses, forming a condensate containing unwanted particles and pathogens that have been removed from the continuing volume of gas; heating the continuing volume of gas; wherein the steps of cooling and heating are alternated; and collecting the condensate in a collection reservoir.

The method may further comprise the step of irradiating the continuing volume of gas with UV-A, UV-B, or UV-C light energy such that the continuing volume of gas receives at least 10-20 mJ/cm2 dosage.

The method may further comprise the step of irradiating the continuing volume of gas with UV-A, UV-B, or UV-C light energy such that the continuing volume of gas receives at least 10-200 mJ/cm2 dosage.

The method may further comprise the step of maintaining the condensate in the collection reservoir at a temperature equal to or greater than 56° C.

In embodiments, the step of cooling the continuing volume of gas may be performed by causing the continuing volume of gas to come into thermal communication with a cold surface at between 0° C. to 15° C., inclusive. In embodiments, the step of heating the continuing volume of gas may be performed by causing the continuing volume of gas to come into thermal communication with a hot surface at between 0° C. to 15° C., inclusive.

In embodiments, the invention may comprise a method for removing unwanted particles and pathogens from a continuing volume of gas, comprising the steps of: cooling the continuing volume of gas such that water in the air condenses, forming a condensate containing the unwanted particles and pathogens that have been re-moved from the continuing volume of gas; collecting the condensate; applying the condensate to at least one hot surface, and causing water forming the condensate to evaporate, leaving the unwanted particles and pathogens on the hot surface. The at least one hot surface may be at a temperature in the range of 50° C. to 60° C., inclusive. The method may further comprise the step of removing the unwanted particles and neutralized pathogens from the hot surface.

In embodiments, the method comprises the step of cooling the continuing volume of gas may be performed by passing said continuing volume of gas between opposing cold surfaces of at least one thermoelectric module pair, wherein at least a portion of said continuing volume of gas is in thermal communication with at least one of said cold surfaces.

In embodiments the cold surfaces may be at a temperature in a range between 0° C. and 10° C., inclusive.

In embodiments the step of applying the condensate to at least one hot surface is performed by spraying.

In embodiments the step of applying the condensate to at least one hot surface is performed by wicking.

In embodiments the method may further comprise the step of ionizing said continuing volume of gas, so that unwanted materials in the gas are more likely to be carried out of the gas by the condensate.

In embodiments the method may further comprise the step of irradiating the continuing volume gas with UV-A, UV-B, or UV-C light energy such that the continuing volume of gas receives at least 10-20 mJ/cm2 dosage.

The method may further comprise the step of irradiating said air with UV-A, UV-B, or UV-C light energy such that the continuing volume of gas receives at least 10-200 mJ/cm2 dosage.

The method may further comprise the step of at least partially neutralizing a patho-gen contained in said condensate by causing said condensate to come into contact with a catalytic material.

The method may further include at least a portion of said at least one hot surface comprising a catalytic material.

The method may further include the condensate collection reservoir containing the condensate comprising a catalytic material.

A further advantage of the present invention over systems and method of the prior art is that the unwanted particles and pathogens that remain on the hot surfaces have been neutralized such that no active biohazard wasted is produced.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating exemplary embodiments of the invention and are not to be construed as limiting the invention. In the drawings.

In the figures, like item callouts refer to like elements.

Figure 1:
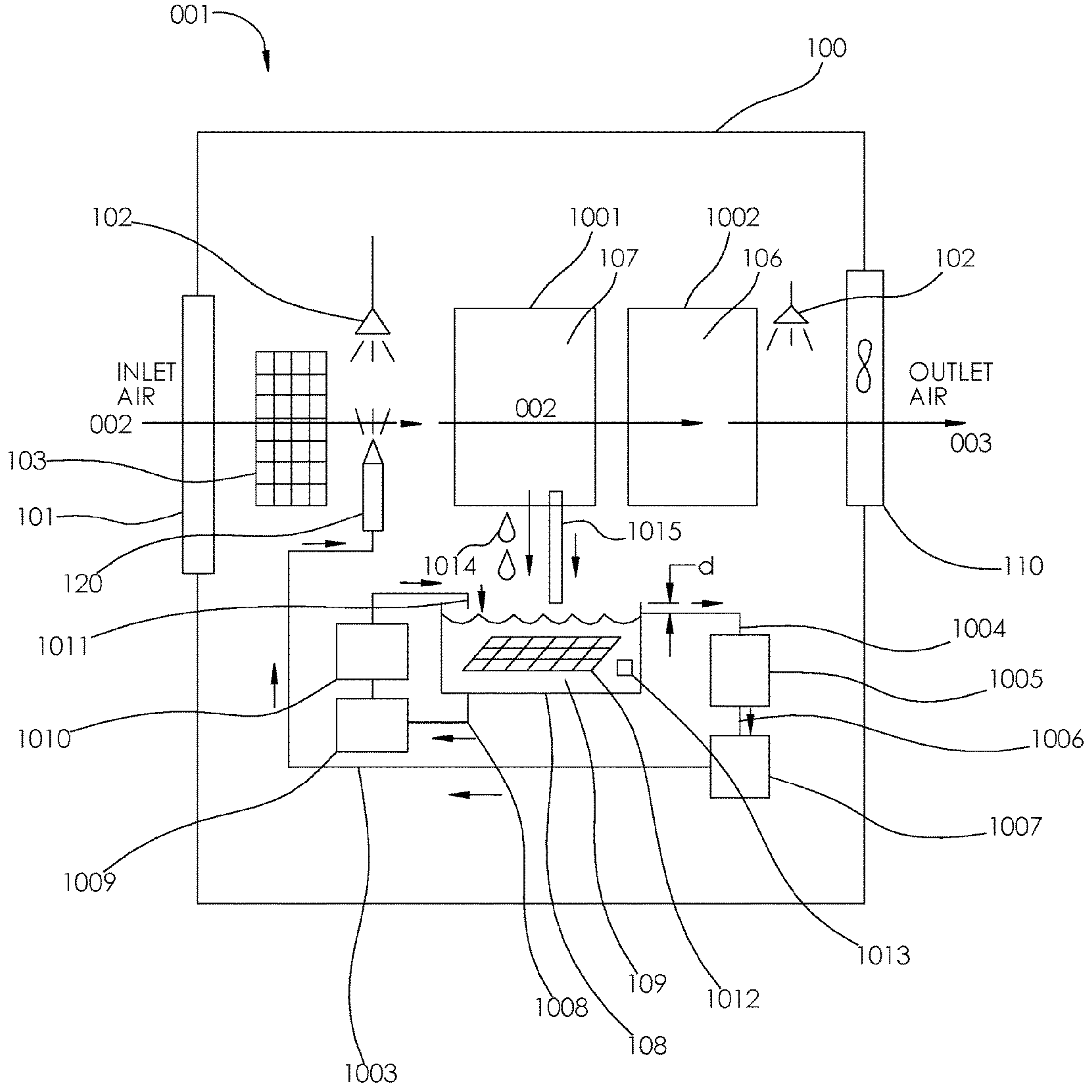
FIG. 1 depicts an exemplary embodiment of the invention, showing in schematic fashion the elements of the embodiment.

The various embodiments of the invention may comprise any or all of the features of the invention described herein, in any number, and in any combination.

DETAILED DESCRIPTION OF THE INVENTION

The following documentation provides a detailed description of the invention.

Although a detailed description as provided in this application contains many specifics for the purposes of illustration, anyone of ordinary skill in the art will appreciate that many variations and alterations to the following details are within the scope of the invention. Accordingly, the following preferred embodiments of the invention are set forth without any loss of generality to, and without imposing limitations upon, the claimed invention. Thus, the scope of the invention should be determined by the appended claims and their legal equivalents, and not merely by the preferred examples or embodiments given.

"Peltier effect" as used herein includes within its meaning the effect produced when an electric current is passed through a circuit of a thermocouple causing heat to be evolved at one junction and absorbed at the other junction. The Peltier effect is the presence of heating or cooling at an electrified junction of two different conductors. When a current is made to flow through a junction between two conductors A and B, heat may be generated or removed at the junction. The Peltier heat generated at the junction per unit time may be characterized as:

$$\dot{Q}=(\Pi_A-\Pi_B)I$$

where $\pi_A$ and $\pi_B$ are the Peltier coefficients of conductors A and B, and I is the electric current (from A to B). The total heat generated is not determined by the Peltier effect alone, as it may also be influenced by Joule heating and thermal-gradient effects (see below). The Peltier coefficients represent how much heat is carried per unit charge. Since charge current must be continuous across a junction, the associated heat flow will develop a discontinuity if $\pi_A$ and $\pi_B$ are different. The Peltier effect can be considered as the back-action counterpart to the Seebeck effect (analogous to the back-EMF in magnetic induction): if a simple thermoelectric circuit is closed, then the Seebeck effect will drive a current, which in turn (by the Peltier effect) will always transfer heat from the hot to the cold junction. Thermoelectric heat pumps exploit this phenomenon, as do thermoelectric cooling devices found in refrigerators.

"Peltier device" as used herein includes within its meaning devices that may comprise one or more junctions in series through which an electric current I is driven, resulting in a temperature difference between first and second exterior surfaces of the device. In embodiments, the first and second exterior surfaces may experience temperature differences of up to and exceeding 60° C. I.e., in an exemplary device, the first surface may maintain a temperature of 0° C., and the second surface may maintain a temperature of 60° C., or as otherwise defined in this disclosure, in the presence of electric current I. The first and second surfaces may be thermally conductive materials such as a metal. Individual Peltier devices may be stacked so as to operate in series to provide a greater temperature differential across the first and second surface than can reasonably be achieved in single Peltier device. In such cases, the first surface of a first Peltier device may be in thermal communication (for example, through physical contact) with a second surface of a second Peltier device (again, for example, through physical contact) and so on, creating a stack of Peltier devices in a series thermal communication arrangement, the hot side of one Peltier device in physical contact with the cold side of an adjacent Peltier device, and so on, achieving a greater temperature differential across the first outside surface and second outside surface than can reasonably be achieved in single Peltier device. It is an advantage of Peltier devices that they have no moving parts, and are thus not susceptible to the failure mechanisms of other temperature differential producing systems such as conventional vapor-compression systems that use piston compressors, mechanical relays, high pressure tubing and interconnects, and the mechanical components that are prone to wear-out, fatigue, environmental decomposition (e.g. rust and corrosion) and other failure modes.

"Pathogen" as used herein includes within its meaning any bacterium, virus, or other microorganism that can cause disease in humans or non-humans, including airborne pathogens such as viruses, for example and not by way of limitation, the coronavirus that causes coronavirus disease 2019 (COVID-19).

"Hydrophobic coating" as used herein includes within its meaning any coating that repels water, allowing the water to be readily removed from a surface comprising the hydrophobic coating. "Hydrophobic coating" includes within its meaning all coatings commonly designated as hydrophobic or superhydrophobic. Water, when applied to a surface coated with a hydrophobic coating, forms droplets that are easily motivated along the surface when acted upon by a force such as the force of gravity or forces produced when the water is acted upon by forced air, such as from a fan or blower. Some hydrophobic coatings comprise composite materials where one component provides the roughness and the other provides low surface energy. One non-limiting basis of hydrophobicity is the creation of recessed areas on a surface whose wetting expends more energy than bridging the recesses expends. This so-called Wenzel-effect surface or lotus (flower) effect surface has less contact area by an amount proportional to the recessed area, giving it a high contact angle. The recessed surface has a proportionately diminished attraction foreign liquids or solids. Hydrophobic coatings include but are not limited to manganese oxide polystyrene (MnO2/PS) nano-composites, Zinc oxide polystyrene (ZnO/PS) nano-composites, precipitated calcium carbonate, carbon nano-tube structures, silica nano-coating, fluorinated silanes and fluoropolymer coatings, paraffin, TFE telomer, perfluoroalkyl, perfluoropolyether and RF plasma, nanopin film, any low-energy surface coating.

"Catalytic material" as used herein means any material that is useful and operable for neutralizing a pathogen. In different applications of the system and method of the invention, different catalytic materials may be used for specific pathogens. For example, in Covid-19 application, specific catalytic materials known to be effective for neutralizing the SARS-CoV-2 virion, rendering it less virulent or transmissible, may be utilized. In other applications directed towards other pathogens, other catalytic materials known to be effective for neutralizing those pathogens may be utilized in the invention. Examples of catalytic materials include but are not limited to materials that comprise cuprous oxide (Cu2O) particles bound with polyurethane, and including copper, silver, ionic silver, titanium, zinc and their oxides.

"Unwanted materials" includes any material that is present in the gas to be cleaned 002 such as, for instance, suspended biologic, organic or inorganic particles, pathogens (such as, for example, viruses or bacteria), smoke particles, dust, pollen, chemical particles, or any other substance which is desired to be removed from the gas to be cleaned 002.

"Gas" as used herein includes within its meaning any gas, or combination or mixture of gasses, including air. Thus, "gas" includes within its meaning, but is not limited to, air. As used in this disclosure, "gas" and "air" may be used interchangeably to mean any gas or combination of gases, including but not limited to air.

As used herein "reservoir" includes within its meaning tanks, vessels, either open or closed, and containers of any type.

As used herein "continuing volume of gas" refers to the gas, which may be air, that is being motivated through the enclosure of the system, from which it is desired to remove unwanted materials.

Referring now to FIG. 1, an exemplary embodiment of the invention 001 for removing unwanted materials from a volume of gas is depicted. FIG. 1 shows, in schematic fashion, the elements of this particular embodiment, which is just one of many embodiments that are within the legal scope of the invention. A gas for which it is desired to remove unwanted materials, 002, may enter enclosure 100 through an optional filter 101 that removes some, or most, of the dust contained in gas 002. The gas may be motivated through enclosure 100 by any combination of fans or blowers, such as fan 110. Gas 002 then may pass through, or in proximity to, an ionizing apparatus 103, such as, for example, an ionizing grid, that causes ions to be formed in gas 002. As an example, ionizing apparatus 103 may comprise opposing conductive plates, with a voltage applied across the plates with the gas passes between or through the plates. While any apparatus that cause ions to be formed in gas 002 may comprise ionizer 103, an ionizing grid allows gas 002 to pass through the grid and to be efficiently ionized without greatly impeding the movement of gas 002. In embodiments, both positive and negative ions may be formed in gas 002 such that the overall charge of the volume of gas 002 in enclosure 100 is charge-neutral. The ionizing apparatus 103 is not necessarily present in all embodiments of the system and method of the invention. I.e., it is optional, however, when present it enables greater effective of removing unwanted materials from gas 002.

Still referring to FIG. 1, gas 002 may next be irradiated by ultraviolet (UV) light energy, or more specifically ultraviolet-C (UVC, 200 nm-280 nm wavelength), UV-B (280 nm-320 nm), or UV-A (320 nm-400 nm) light, or any combination thereof, from one or a plurality of light sources 102. The light energy from light sources 102 operates to render pathogens in gas 002 inoperative by destroying the ability of such pathogens to reproduce, by causing photochemical reactions in nucleic acids (DNA & RNA), by causes oxidation of proteins and lipids causing cell death, or by inhibiting photo-reactivation, or any combination of the foregoing, among other effects.

Still referring to FIG. 1, gas 002 may also be humidified by a mister, atomizing sprayer, ultrasonic nebulizer or humidifier, 120, that operates to increase the amount of liquid being carried by gas 002. When gas 002 is air, mister or humidifier 120 operates to increase the amount of liquid carried in the air. As an example, mister or humidifier 120 may be an ultrasonic nebulizer that is fed from any source of water or liquid, and which operates to increase the amount of water in gas 002 by using vibrations of a piezoelectric crystal driven by an alternating electrical field to create cavitation in the liquid (which may be water) causing liquid droplets to be generated, which increases the amount of water in gas 002. In a next step, gas 002 will be cooled, reducing its ability to carry the liquid, causing condensate 109 to form, to which unwanted material particles in gas 002 are attached, resulting in the removal of unwanted materials from gas 002 as they are carried out the gas when the condensate forms. And so, by adding liquid (which may be water) to gas 002 through misting, nebulization or equivalent means, the effectiveness of the system and method of the invention is increased, as the amount of liquid that is precipitated from gas 002 when it is cooled in the next step is increased.

Still referring to FIG. 1, gas 002 may then be motivated to come into thermal communication with "cold" surface 107, which is at a temperature lower than gas 002, by passing in proximity to, or impinging or impacting, surface 107. When gas 002 comes into thermal communication with cold surface 107, the temperature of gas 002 is lowered, reducing its ability to hold liquid, and causing condensate 109 to form and to be communicated to and collect in condensate collection reservoir 108. In any of the embodiments of the invention, condensate 109 may be motived into condensate collection reservoir 108 by dripping 1014, or by wicking, or by being carried by tubing or piping, or channels, which may be microchannels in a plate or other substrate, generally depicted as 1015 (all of the foregoing being "fluid communication means"). When condensate 109 forms, unwanted materials in the gas 002 cling to the condensate, and thus when the condensate is formed and collected, it carries with it the unwanted materials. Thus, these materials have been removed from the gas 002 (i.e. gas 002 has been "cleaned").

Figure 2:
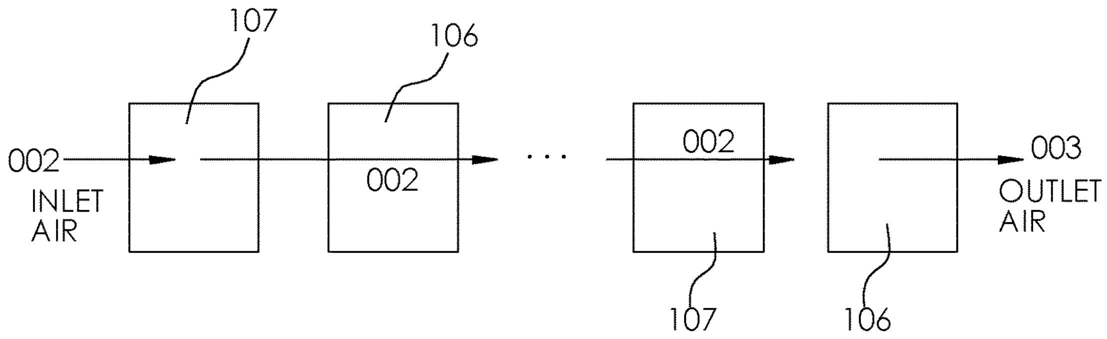
FIG. 2 depicts, schematically, that the invention may comprise any number of hot and/or cold surfaces.

Still referring to FIG. 1, gas 002 may then be motivated to impinge, pass over, or otherwise come into thermal communication with "hot" surface 106, which is at a temperature higher than gas 002, by passing in proximity to, or impinging or impacting, surface 106. When gas 002 comes into thermal communication with surface 106, the temperature of gas 002 is raised, enabling the gas to again optionally be misted, or humidified, using for example one or more additional misters or humidifiers 120 and the process of cooling gas 002 and condensing liquid out of gas 002, and thus further removing remaining unwanted materials that may be still be present in gas 002, may be repeated for any number of cool-condense-heat cycles, each cycle further removing unwanted materials from gas 002 as depicted in FIG. 2. This process may be repeated through successive stages until gas 002 has reached a desired level of unwanted material presence in gas 002, at which point the cleaned gas may exit the enclosure as outlet air 003.

Still referring to FIG. 1, condensate 109 that is collected in collection reservoir 108 may contain pathogens, in some cases at concentrated levels. It is therefore desirable to render such pathogens inert or inoperable, i.e. to neutralize them, so that they cannot cause disease in humans or non-humans. A catalytic mesh material or coating 1012, such as, for example, copper, which has known pathogen neutralizing properties, may be present in collection reservoir 108 for neutralizing pathogens in condensate 109. The effectiveness of such catalytic pathogen neutralizing materials may be increased with increased condensate temperatures, and thus the system of the invention may comprise a first pump 1009 in fluid communication with collection reservoir 108 via fluid communication means, that causes condensate 109 to be pumped from collection reservoir 108 through fluid heater 1010 via fluid communication means, where it exits fluid heater 1010 at a higher temperature than it entered fluid heater 1010. First pump 1009 may be in fluid communication with fluid heater 1010 via fluid communication means. The heated condensate exiting fluid heater 1010 may be returned to collection reservoir 108 via heated condensate return fluid communication means 1011. Thus, condensate 109 in collection reservoir 108 may be heated to increase the effectiveness of the catalytic pathogen neutralizing materials 1012 (which may be, for example, copper mesh or lining), and thereby increasing the effectiveness of neutralizing pathogens in condensate 109. In embodiments, the temperature of condensate 109 in collection reservoir 108 may be controlled to be equal to or greater than 56° C., or in the range of 56° C.-65° C., as 56° C. is an effective temperature for neutralizing pathogens. A temperature sensor 1013, which is in data communication with controller 402 (see FIG. 17), may be present in collection reservoir 108 such that controller 402 (see FIG. 17) is operable to control first pump 1009 and heater 1010 in order to achieve a desired temperature of condensate 109 in collection reservoir 108.

In any embodiments of the system of the invention, cold surfaces 107 may be at any temperature lower than the gas 002 impinging them but ideally are in a range of 0° C. to 15° C., or 0° C. to 10° C. Likewise, in embodiments of the system of the invention, hot surfaces 106 may be any temperature higher than the gas 002 impinging them but ideally are in a range of 40° C. to 60° C., or 50° C. to 70° C., or an overall range of 40° C. to 70° C.

Still referring to FIG. 1, fluid communication means 1004 may be in fluid communication with collection reservoir 108, and may be disposed a distance "d" from the top of collection reservoir 108, such that, when condensate is accumulated in collection reservoir 108 to the point that it reaches a point d from the top of the reservoir, second pump 1005, which is in fluid communication with collection reservoir 108 via fluid communication means 1004, operates to pump condensate from collection reservoir 108 through fluid communication means (for example tubing or piping) 1006 into flash boiler 1007, which elevates the temperature of the condensate 109 passing through flash boiler 1007 to temperatures between 150° F. and 210° F., and in some cases, 180° F. and 190° F. These temperatures operate to neutralize any remaining pathogens in condensate 109 that is heated by flash boiler 1007. The outlet side of flash boiler 1007 is in fluid communication with an inlet port of mister, humidifier, or ultrasonic nebulizer 120 via fluid communication means 1003, which may be, for example, a copper tube to increase pathogen neutralization. Because the temperature of the condensate 109 fed into the mister, humidifier, or ultrasonic nebulizer 120 is elevated, the heated condensate is more easily converted to fine droplets for increasing the amount of fluid in gas 002. Because the heated condensate 109 that is fed into mister, humidifier, or ultrasonic nebulizer 120 has been heated by flash boiler 1007, any pathogens in it have been neutralized, preventing the spread of pathogens into incoming gas 002 by the misting/humidifying/nebulizing process.

Still referring to FIG. 1, the system and method of the invention cause unwanted materials to be removed from gas 002 by condensation, and then to be neutralized as described herein, such that the outlet air 003 exiting enclosure 100 has been cleaned relative to the air in its incoming condition, such that only an acceptable low level of unwanted material remains.

Still referring to FIG. 1, cold surfaces(s) 107 and hot surfaces(s) 106 may be cooled, or heated, respectively, by any known means. For example, cold surface 107 may form a part of a cold surface module 1001 that uses any means of cooling such circulation of cooled fluid and heat exchanger or thermoelectric cooling. Likewise, hot surface 106 may form a part of a hot surface module 1002 that uses any means of heating such circulation of a heated fluid and heat exchanger or resistive electric heating element. Cold surface module 1001 and hot surface module 1002 may each be controllable and may be in communication with controllable power supply such that controller 402 is operable to control the temperatures of cold surfaces(s) 107 and hot surfaces(s) 106.

Referring now to FIG. 2, embodiments of the system and method of the invention may comprise successive steps of cooling via cold surface 107, then heating via hot surface 106, gas 002, for as many repeated cycles as may be necessary to reduce the amount of unwanted materials in gas 002 to an acceptable level. The "acceptable level" may vary depending upon the intended use of gas 002, and the type of unwanted material present in gas 002.

Figure 3:
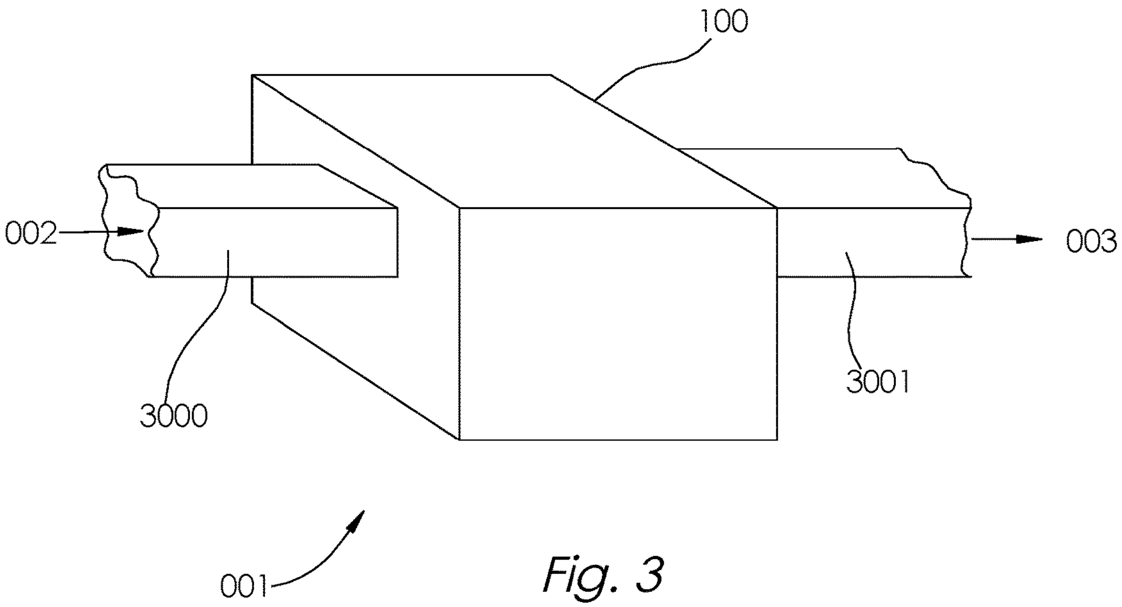
FIG. 3 depicts a perspective view of an embodiment of the invention that is suitable, as an example, for use in the ducting system of a heat, ventilation, and air conditioning ("HVAC") system.

Referring now to FIG. 3, a perspective view of an embodiment of the invention that is suitable, as an example, for use in the ducting system of a heat, ventilation, and air conditioning ("HVAC") system, is depicted. Inlet gas (e.g., air) 002 may enter enclosure 100 via ducting or piping 3000. Gas 002 is treated within enclosure 100 as described herein, and exits as cleaned air 003 via ducting or piping 3001. As an exemplary use case, ducting 001 and 005 may be return or supply HVAC ducting for a facility, building, structure which may be any structure. Thus, the system and method of the invention may be installed in any HVAC system for cleaning air of unwanted materials. As an example, the embodiment of the system of the invention depicted in FIG. 3 may be installed in the HVAC systems of medical facilities, physician's offices, hospitals, rehab facilities, assisted living facilities, or other facilities in order to reduce or stop the spread of disease by airborne pathogens.

Figure 4:
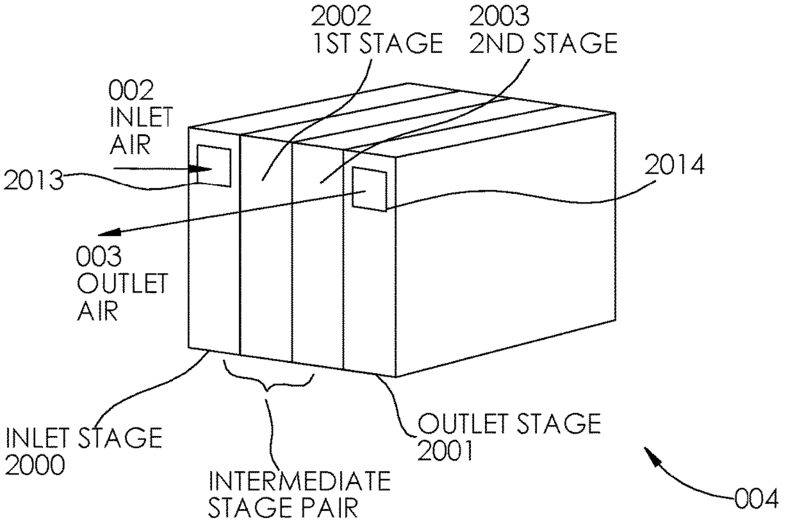
FIG. 4 depicts a perspective view of a multi-stage embodiment of the invention that comprises stackable stages, enabling the constructing of an embodiment of the invention that comprises any desired number of stages. In cases in which unwanted material, such as pathogens, are present in the air to be cleaned 002 in great numbers, additional stages may be employed to achieve a resulting desired low level of pathogens (or other wanted materials) in a particular volume of gas.

Referring now to FIG. 4, a perspective view of a stackable multi-stage embodiment of the invention 004 that comprises stackable gas cleaning stages, enabling the constructing of an embodiment of the invention that comprises any desired number of gas cleaning stages, is depicted. In cases in which unwanted material, such as pathogens, are present in the air to be cleaned 002 in great numbers, a plurality of gas cleaning stages may comprise the invention, each gas cleaning stage removing unwanted material from gas 002, in order to achieve a resulting desired low level of pathogens (or other wanted materials) in gas 002.

Still referring to FIG. 4, an exemplary stackable multi-stage embodiment that comprises four stages—an input stage, a pair of stages forming an intermediate stage pair, and an outlet stage, is depicted. This embodiment is exemplary, because any number of intermediate stage pairs may comprise the stackable multi-stage embodiment. For example, if additional cleaning of gas 002 is desired, a six-stage embodiment, comprising an input stage, a first stage pair, a second intermediate stage pair, and an outlet stage may be employed. An intermediate stage pair may comprise a first intermediate stage and a second ($2^{nd}$) intermediate stage—i.e., each intermediate stage pair may comprise two stages. In FIG. 4, one intermediate stage pair, comprising intermediate first stage 2002 and intermediate stage 2003, is shown. The system and method of the invention may comprise any number of intermediate stage pairs.

Figure 5:
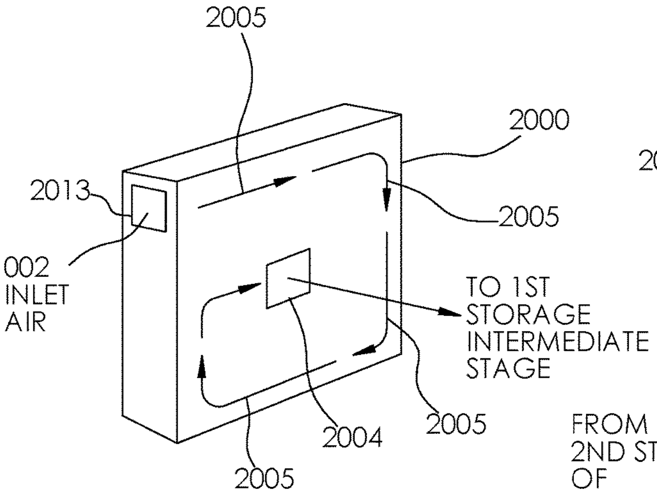
FIG. 5 depicts an exemplary embodiment of an inlet stage of the multi-stage embodiment of the invention depicted in FIG. 4.
Figure 8:
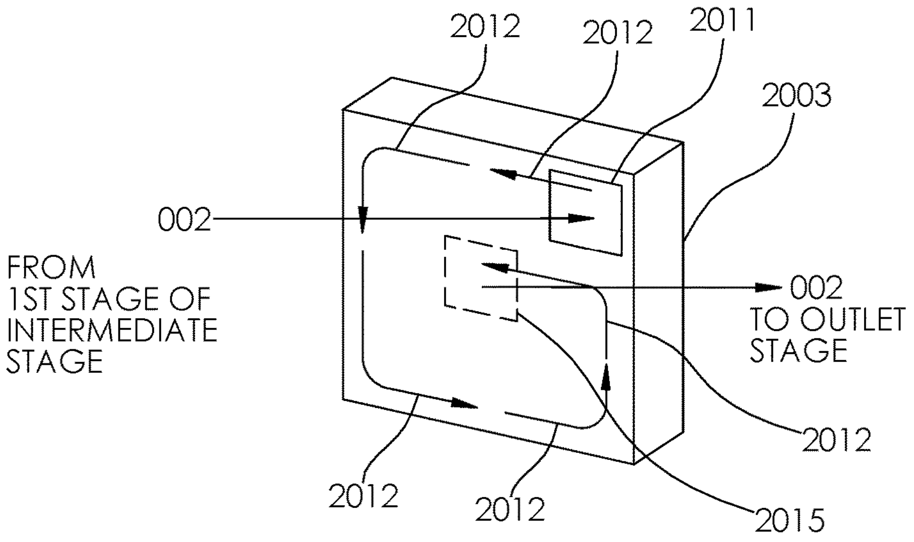
FIG. 8 depicts an exemplary embodiment of a second (2nd) intermediate stage of an intermediate stage pair of the multi-stage embodiment of the invention depicted in FIG. 4.
Figure 9:
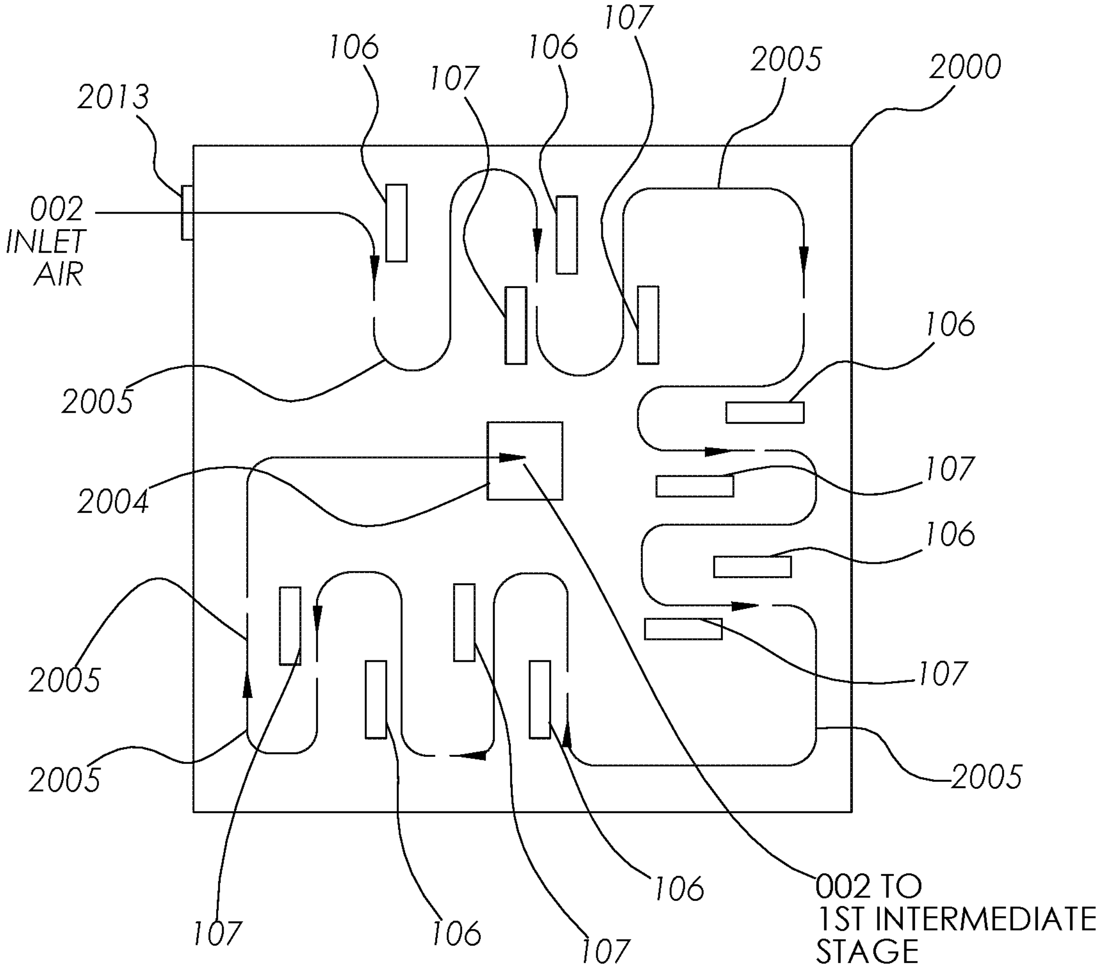
FIG. 9 depicts one of many arrangements of air flow through the exemplary inlet stage depicted in FIG. 5.

Still referring to FIG. 4, gas to be cleaned 002 enters the system through inlet 2013 on inlet stage 2000, circulates among cold surfaces 107 and hot surfaces 106 as depicted in exemplary fashion in FIGS. 5 and 9, and exits inlet stage 2000 such that it enters first ($1^{st}$) intermediate stage 2002. Once in intermediate stage 2002, gas 002 circulates among cold surfaces 107 and hot surfaces 106 as depicted in exemplary fashion in FIGS. 7 and 10, and exits first ($1^{st}$) intermediate stage 2002 such that it enters second (2nd) intermediate stage 2003. Once in second (2nd) intermediate stage 2003, gas 002 circulates among cold surfaces 107 and hot surfaces 106 as depicted in exemplary fashion in FIGS. 8 and 11, and exits second ($2^{nd}$) intermediate stage 2003 such that it enters outlet stage 2001. Once in outlet stage 2001, gas 002 circulates among cold surfaces 107 and hot surfaces 106 as depicted in exemplary fashion in FIGS. 6 and 12, and exits second ($2^{nd}$) intermediate stage 2003 as cleaned gas (which may be air, in exemplary cases). It can be seen that, by adding additional intermediate stage pairs, a desired level of removal of unwanted material from gas 002 may be achieved. In embodiments, there may be no intermediate stage pairs, one intermediate stage pair, two intermediate stage pairs, or any number of intermediate stage pairs. In this sense, the embodiment of the invention depicted in FIGS. 4-12 is "stackable", meaning that it may comprise no intermediate stage pairs or any number of intermediate stage pairs. In FIGS. 4-12, the collection reservoir 108, fluid communication means, misters 120 (which may be ultrasonic nebulizers), UV, UVA, UVB, and UCV lights 102, ionizer 103, first pump 1009 and heater 1010, and second pump 1005 and flash boiler 1007, have not been shown for clarity. It is to be understood that these elements may be located within any of the stages, in accordance with the disclosure herein, in any quantity, and in any arrangement to achieve the objectives described herein.

Referring now to FIGS. 5 and 9, the operation of an exemplary embodiment of inlet stage 2000 is described. Gas to be cleaned 002 may enter inlet stage 2000 though inlet 2013 and circulate through inlet stage 2000 in the direction shown by arrows 2005, and then exit inlet stage 2000 through inlet stage outlet opening 2004. While circulating through inlet stage 2000 in the direction of arrows 2005, gas 002 may, more specifically, circulate through and among cold surfaces 107 and hot surfaces 106 as shown in more detail in FIG. 9, such that gas 002 is in thermal communication with at least one or a plurality of cold surfaces 107 and at least one or a plurality of hot surfaces 106. When gas 002 is cooled by the at least one or a plurality of cold surfaces 107, condensate 109 is caused to form as water in the air condenses, the condensate 109 carrying with it unwanted material (such as, for example, pathogens) that was present in gas 002. Condensate 109 is collected, and the pathogens in condensate 109 may be neutralized, as described elsewhere in this disclosure. Thus, as gas 002 passes through inlet stage 2000, unwanted materials are removed from gas 002; i.e., it is cleaned.

Figure 7:
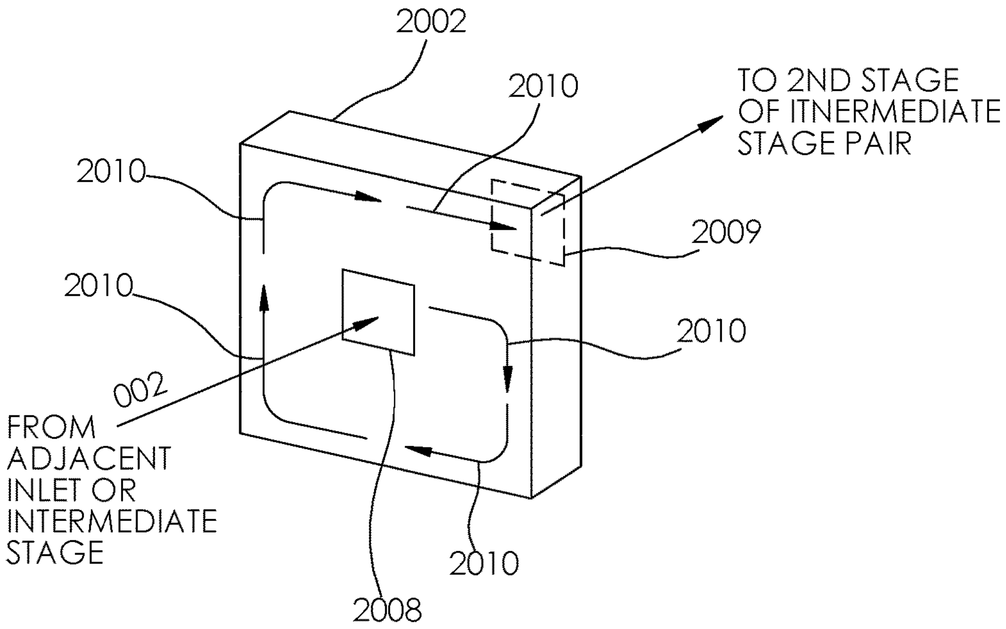
FIG. 7 depicts an exemplary embodiment of a first (1$^{st}$) intermediate stage of an intermediate stage pair of the multi-stage embodiment of the invention depicted in FIG. 4.
Figure 10:
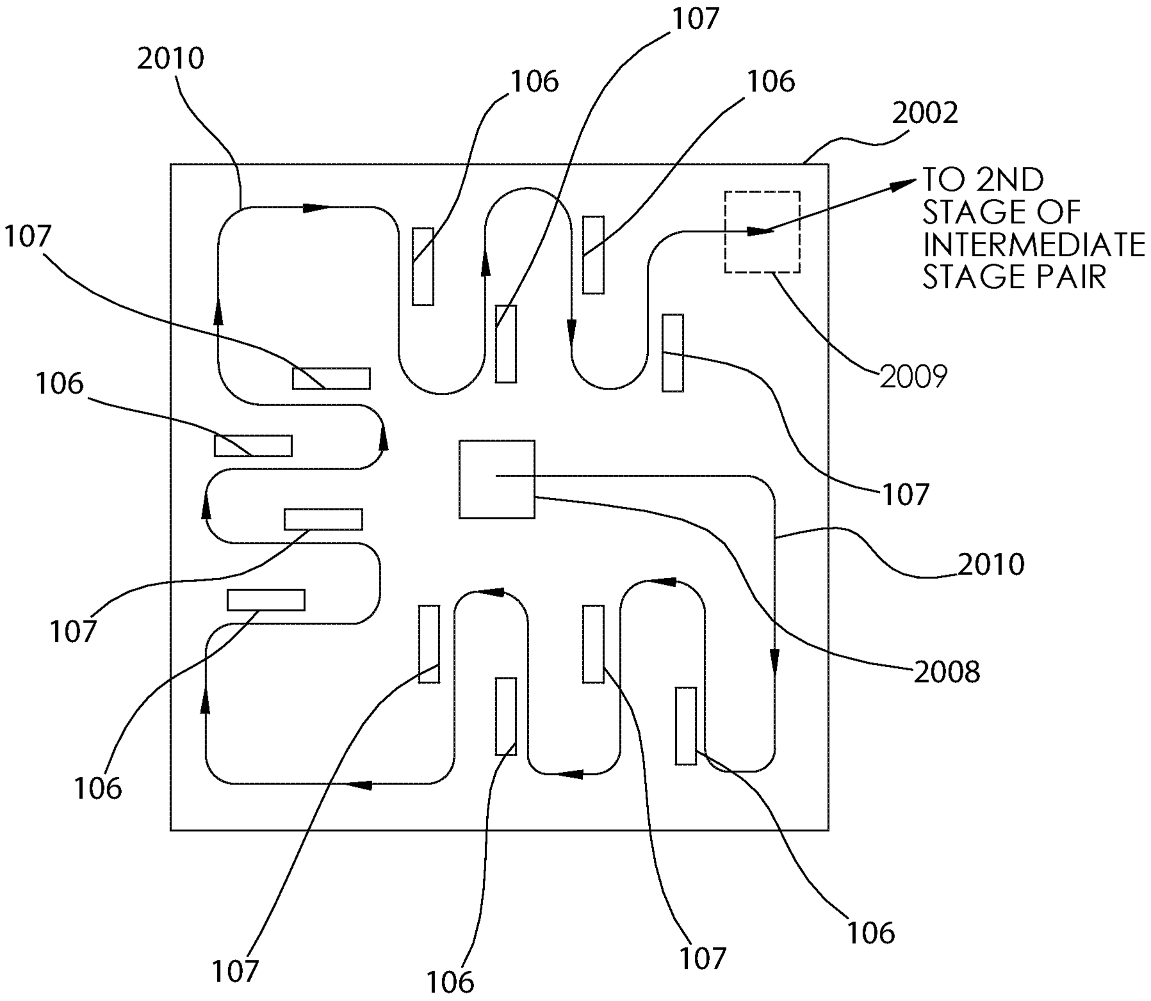
FIG. 10 depicts one of many arrangements of air flow through the exemplary first (1$^{st}$) intermediate stage of an intermediate stage pair depicted in FIG. 7.

Referring now to FIGS. 7 and 10, the operation of an exemplary embodiment of first ($1^{st}$) intermediate stage 2002 is described. Gas 002 may enter first ($1^{st}$) intermediate stage 2002 though first intermediate stage inlet 2008, which may be aligned with inlet stage outlet opening 2004 when inlet stage 2000 and first intermediate stage 2002 are connected, or stacked. Gas 002 may then circulate through first ($1^{st}$) intermediate stage 2002 in the direction shown by arrows 2010, and then exit first ($1^{st}$) intermediate stage 2002 through first intermediate stage outlet opening 2009. While circulating through first (It) intermediate stage 2002 in the direction of arrows 2010, gas 002 may, more specifically, circulate through and among cold surfaces 107 and hot surfaces 106 as shown in more detail in FIG. 10, such that gas 002 is in thermal communication with at least one or a plurality of cold surfaces 107 and at least one or a plurality of hot surfaces 106. When gas 002 is cooled by the at least one or a plurality of cold surfaces 107, condensate 109 is caused to form as water in the air condenses, the condensate 109 carrying with it unwanted material (such as, for example, pathogens) that was present in gas 002. Condensate 109 is collected, and the pathogens in condensate 109 may be neutralized, as described elsewhere in this disclosure. Thus, as gas 002 passes through first ($1^{st}$) intermediate stage 2002, unwanted materials are removed from gas 002; i.e., it is cleaned.

Figure 11:
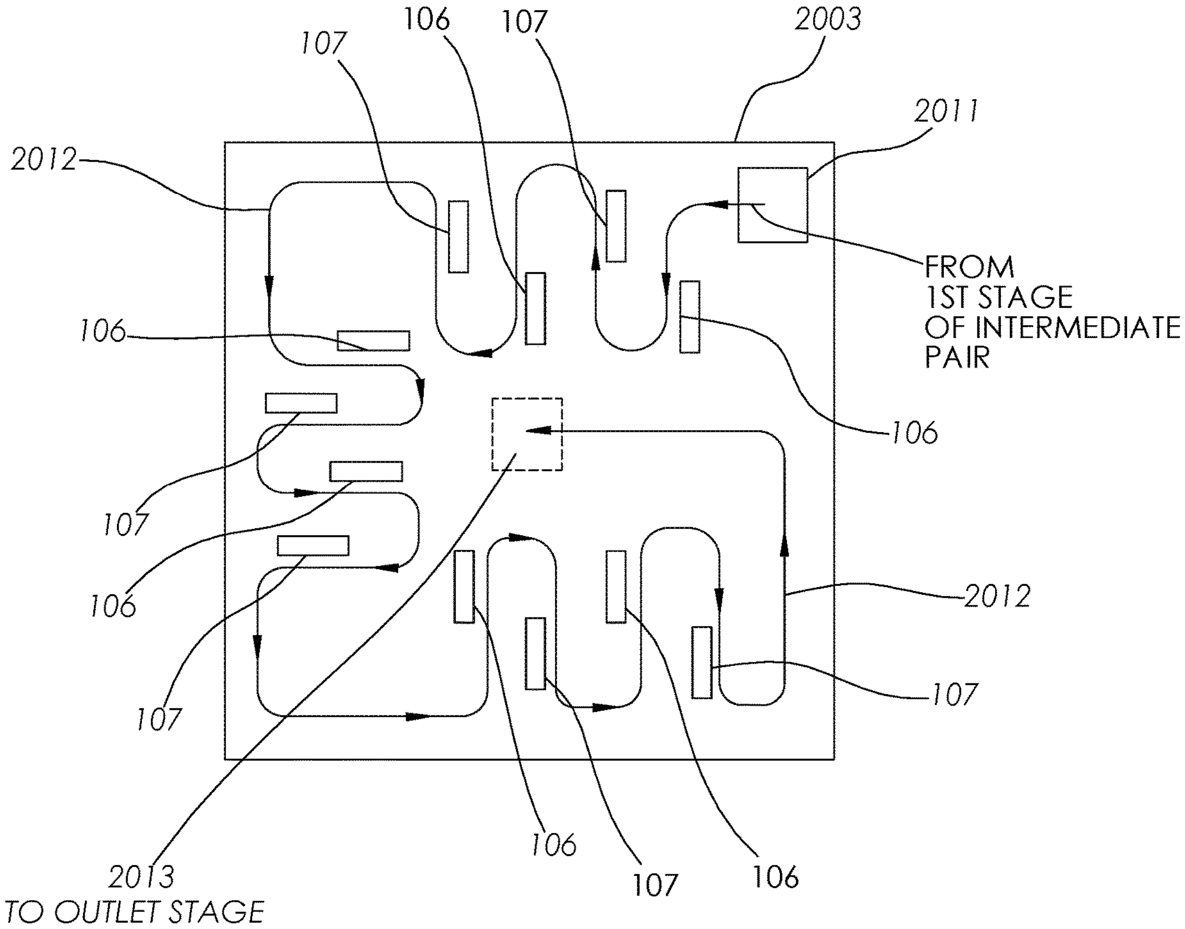
FIG. 11 depicts one of many arrangements of air flow through the exemplary second (2nd) intermediate stage of an intermediate stage pair depicted in FIG. 8.

Referring now to FIGS. 8 and 11, the operation of an exemplary embodiment of second ($2^{nd}$) intermediate stage 2003 is described. Gas 002 may enter second ($2^{nd}$) intermediate stage 2003 though second intermediate stage inlet 2011, which may be aligned with first intermediate stage outlet opening 2009 when first ($1^{st}$) intermediate stage 2002 and second intermediate stage 2003 are connected, or stacked. Gas 002 may then circulate through second ($2^{nd}$) intermediate stage 2003 in the direction shown by arrows 2012, and then exit second ($2^{nd}$) intermediate stage 2003 through second intermediate stage outlet opening 2015. While circulating through second ($2^{nd}$) intermediate stage 2003 in the direction of arrows 2012, gas 002 may, more specifically, circulate through and among cold surfaces 107 and hot surfaces 106 as shown in more detail in FIG. 11, such that gas 002 is in thermal communication with at least one or a plurality of cold surfaces 107 and at least one or a plurality of hot surfaces 106. When gas 002 is cooled by the at least one or a plurality of cold surfaces 107, condensate 109 is caused to form as water in the air condenses, the condensate 109 carrying with it unwanted material (such as, for example, pathogens) that was present in gas 002. Condensate 109 is collected, and the pathogens in condensate 109 may be neutralized, as described elsewhere in this disclosure. Thus, as gas 002 passes through second ($2^{nd}$) intermediate stage 2003, unwanted materials are removed from gas 002; i.e., it is cleaned.

Figure 6:
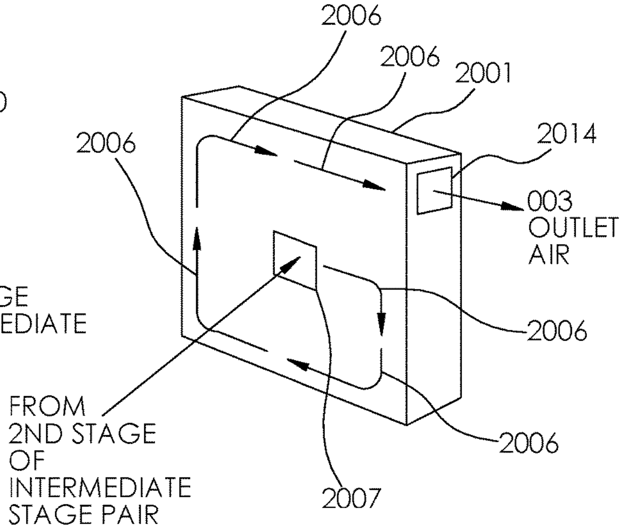
FIG. 6 depicts an exemplary embodiment of an outlet stage of the multi-stage embodiment of the invention depicted in FIG. 4.
Figure 12:
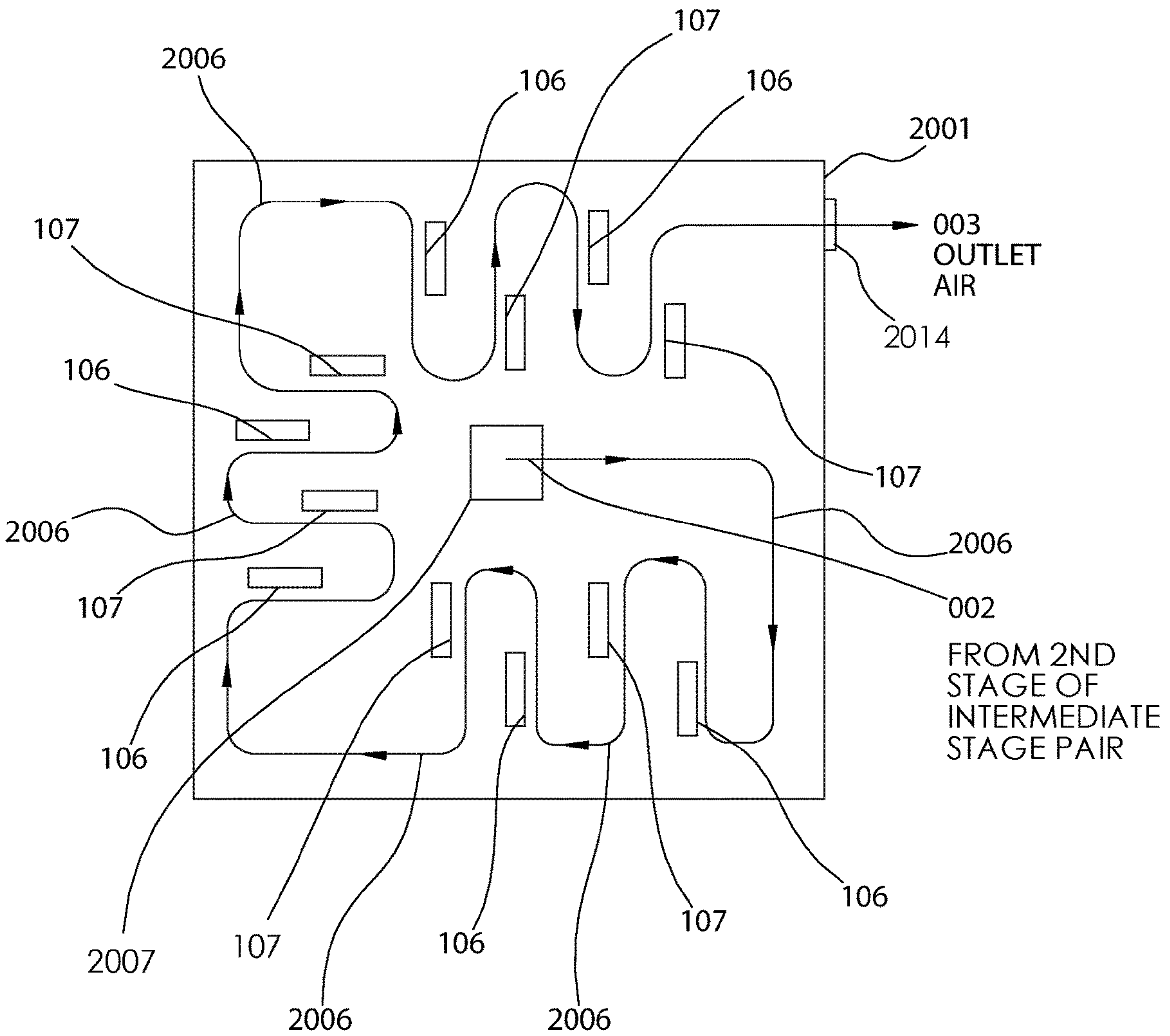
FIG. 12 depicts one of many arrangements of air flow through the exemplary outlet stage depicted in FIG. 6.

Referring now to FIGS. 6 and 12, the operation of an exemplary embodiment of outlet stage 2001 is described. Gas 002 may enter outlet stage 2001 though outlet stage inlet 2007, which may be aligned with second intermediate stage outlet opening 2015 when second ($2^{nd}$) intermediate stage 2003 and outlet stage 2001 are connected, or stacked. Gas 002 may then circulate through outlet stage 2001 in the direction shown by arrows 2006, and then exit outlet stage 2001 through outlet stage outlet opening 2014. While circulating through second outlet stage 2001 in the direction of arrows 2006, gas 002 may, more specifically, circulate through and among cold surfaces 107 and hot surfaces 106 as shown in more detail in FIG. 12, such that gas 002 is in thermal communication with at least one or a plurality of cold surfaces 107 and at least one or a plurality of hot surfaces 106. When gas 002 is cooled by the at least one or a plurality of cold surfaces 107, condensate 109 is caused to form as water in the air condenses, the condensate 109 carrying with it unwanted material (such as, for example, pathogens) that was present in gas 002. Condensate 109 is collected, and the pathogens in condensate 109 may be neutralized, as described elsewhere in this disclosure. Thus, as gas 002 passes through outlet stage 2001, unwanted materials are removed from gas 002; i.e., it is cleaned.

Referring to FIGS. 4-12, each of the stages may comprise at least one fan or blower, and one or a plurality of baffles, plenums, or other structures, for motivating and directing the flow of a continuing volume of gas 002 through the stages as depicted in the figures.

Figure 13:
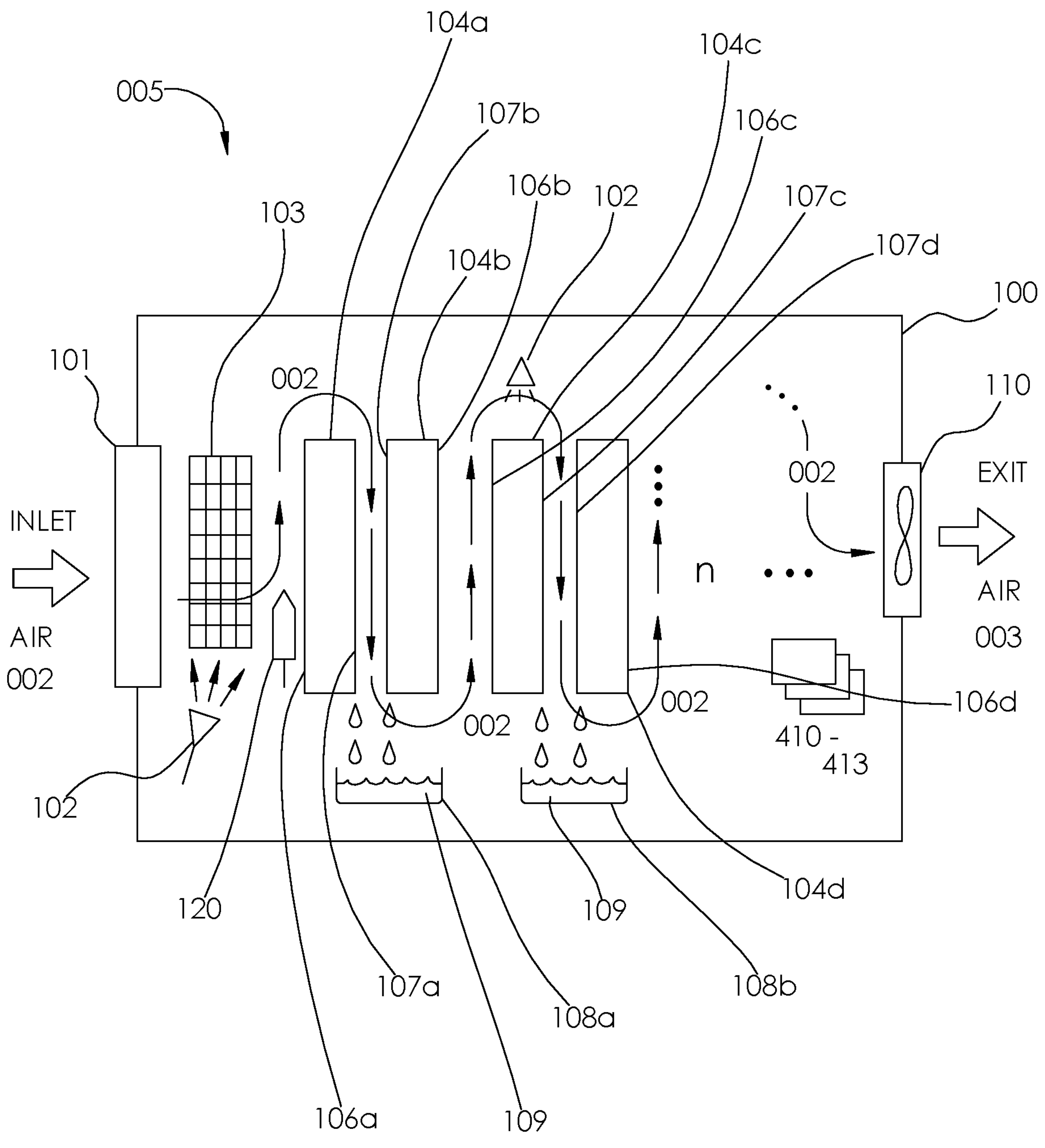
FIG. 13 depicts an embodiment of a system of the invention comprising a plurality of thermoelectric modules disposed within an enclosure for carrying out the method of the invention.

Referring now to FIG. 13, an embodiment of the system of the invention 005 that comprises thermoelectric modules is depicted. Gas 002, which may be, in embodiments, a volume of air, may pass through the system of the invention. Gas 002 may be continuously motivated by one or more fans or blowers 110 through an enclosure 100 where gas 002 encounters the various elements of the system that are operable to remove unwanted material from the air. The flow of gas 002 through enclosure 100, in which gas 002 is directed such that it encounters the various elements of the invention as described herein, is depicted by the arrows in the figure.

Still referring to FIG. 13, in an embodiment, the system of the invention may comprise inlet filter 101 that removes most of the dust contained in gas 002. This step mitigates particle contamination of the inside of the system, which serves to extend the time between system maintenance or cleaning procedures. Inlet filter 101 may be a coarse particle filter or impingement filter. Alternatively, inlet filter 101 may be an ionic filter that operates by ionizing the incoming gas 002 such that dust and other coarse particles are electrically charged and are collected on receiving charged surfaces. Further, in an embodiment, an ionic inlet filter 101 may comprise an anode followed by an ionization zone, followed by a drift zone, followed by a cathode. In such embodiments, ions are motivated from anode to cathode due the electrostatic force exerted on the ions by the electric field generated between the anode and the cathode. As the ions are motivated in the direction of the cathode, they impact air molecules, causing a flow of air in the direction of the cathode. Thus, in an embodiment of inlet filter 101, an ionic filter may also comprise an ionic fan that is operable to motivate air 002 through enclosure 100 such that it impacts and is cooled by the cold surfaces 107 as described herein.

Still referring to FIG. 13, embodiments of the invention may further comprise one or more ionizing elements 103, as described elsewhere herein, such that when gas 003 passes through, or in proximity to, ionizing element 103, unwanted materials in gas 002 are charged with an electric charge, thus increasing their affinity to attach to condensate 109 and thus to be removed more efficiently from gas 002.

Still referring to FIG. 13, embodiments of the invention may further comprise one or more water misters 120, which may be an ultrasonic nebulizer or any other fluid mister element, that serves to provide water molecules and droplets for absorption by gas 002, increasing the amount of water in gas 002, thus increasing the amount of condensate 109 that is formed when gas 002 comes into thermal communication with cold surfaces 107. In embodiments, water may be pumped through misters 120 forming droplets of about a micron in size by venturi effect. Misters, or nebulizers, 120 may also operate as described elsewhere herein. When humidity is low, adding water to gas 002 by misting or nebulizing is even more important, such as when the invention is used in dry climates. Misting, or nebulization, of water into gas 002 may occur at any location within the enclosure, including but not limited to following the inlet filter 101. The gas 002 may also be ionized by any type of ionizing element such as, for example, a high voltage probe, wire, or nanotextured surface, or as described elsewhere herein. In this manner, it may be ensured that the humidity of the gas 002 to be cleaned is high enough to achieve a high rate or volume of condensation when gas 002 comes into thermal communication with cold surfaces 106. The ultrasonic nebulizer(s) 120 may generate a fine water mist that is injected into the volume of air that provides many (at least several million per cubic foot) sites for an airborne unwanted particle or pathogen contained within the volume of air to be adsorbed into. The system may comprise any number of misters or ultrasonic nebulizers 120. Each mister or ultrasonic nebulizer may be connected to a liquid (e.g. water) supply, and to pump and fluid communication means such as piping, tubing microchannels, wicking materials, or any other means of communicating a fluid from one point to another.

Still referring to the embodiment of FIG. 13, air 002 may be directed by a physical configuration of air flow pathways that may include any number or combination of baffles, plenums, pathways or other structures within enclosure 100 such that air 002 comes into contact as described herein with the surfaces of thermoelectric modules 104 (which may be, in embodiments, modules that convert electric energy to heat energy, and vice versa, using the Peltier effect such as in a Peltier module) that may be used to cause a heat flux resulting in cold surfaces 107 and hot surfaces 106. The gas 002 from which unwanted material is desired to be removed 002 may optionally first be heated by passing it over hot surface 106*a* of a first thermoelectric module 104*a*, causing the temperature of gas 002 to be raised. Gas 002 may then then motivated and directed such that it is passed between, and in contact with, cold surfaces 107*a* of first thermoelectric module 104*a* and cold surface 107*b* of second thermoelectric module 104*b* where it is cooled, causing water in the air 002 to condense and precipitate in the form of condensate 109 on the surface of, or in the vicinity of, cold surfaces 107*a* and 107*b*. When the water in gas 002 condenses, it forms condensate 109 that drips down, or is otherwise communicated, from cold surface 107*a* of first thermoelectric module 104*a* and from cold surface 107*b* of second thermoelectric module 104*b* and is collected into a first collection reservoir 108*a*. Condensate 109 contains unwanted materials, such as particles and pathogens, that were attached to water molecules in gas 002 prior to cooling. Thus, condensate 109 contains unwanted particles and pathogens that have been removed from gas 002 through condensation of water molecules in air 002. Thermoelectric modules 104*a* and 104*b* form a first thermoelectric module pair.

Still referring to FIG. 13, in embodiments, each thermoelectric module pair has a dedicated collection reservoir 108 so that condensate 109 that is collected from the water condensed from gas 002 is successively cleaner, i.e., contains fewer unwanted materials per volume of air, with each succeeding thermoelectric module pair stage.

Still referring to FIG. 13, air 002 may then continue to be directed and motivated along and between a hot surface 106*b* of thermoelectric module 104*b* and a hot surface 106*c* of thermoelectric module 104*c* where the air 002 is heated. At this point, an optional micro water spray or ultrasonic nebulizer 120 may be employed to increase the humidity of air 002 as it is heated, providing an increased number of water molecules in air 002 to which unwanted particles and pathogens remaining in air 002 may attach, so that the process of cooling-condensing-collecting condensate containing the unwanted particles and pathogens can be repeated in following stages of thermoelectric module pairs. Air 002 is heated as it passes along and between, in thermal communication with, hot surface 106*b* of thermoelectric module 104*b* and a hot surface 106*c* of thermoelectric module 104*c*. Then air is then directed and motivated to pass between, and in thermal communication with, the cold surfaces 107*c* and 107*d* of second thermoelectric module pair 104*c* and 104*d*, where the condensate 109 is again formed when the cooling of air 002 as it passes between cold surfaces 107*c* and 107*d* of second thermoelectric module pair 104*c* and 104*d*. Condensate 109 drips, in embodiments under the force of gravity, but, in embodiments, by wicking or other means, into collection reservoir 108*b*. And so on, for any number of thermoelectric module pairs.

Still referring to FIG. 13, gas 002 from which unwanted particles and pathogens has been removed exits enclosure 100, providing clean, safe air into the local environment, or alternatively cleaned air 002 may be ducted to another room, enclosed space or volume, or may otherwise be directed to a desired location using known ducting airflow management devices and methods.

Still referring to FIG. 13, one or more fans or blowers 110, of number or type and disposed within enclosure 100 at any location and orientation, may be utilized to motivate gas 002 through the enclosure 100.

Still referring to FIG. 13, in embodiments, the system of the invention may comprise any number n of thermoelectric module pairs (the thermoelectric module pairs are described in further detail below in relation to FIG. 3, and elsewhere herein), allowing a plurality of n stages of cooling-condensing-collecting condensate stages, each stage resulting in air that has successively fewer unwanted particles or pathogens contained therein.

Still referring to FIG. 13, in any of the embodiments of the system and method, sensors 410-413 may be used to determine the condensate 109 level(s) in collection reservoirs 108, so that the heat balance of the thermoelectric modules (or, in non-thermoelectric module embodiments, the hot and cold surfaces) may be adjusted and controlled, for example by controlling current I as described below, to prevent an overflow of water due to excess condensation of the water in air 002, or, to prevent the drying out of the collection reservoir 108. Further, the system and method of the invention may comprise any number of sensors 410 for determining air flow, any number of sensors 411 for determining temperature, and any number of sensors 412 for determining humidity at any location, or on any element, within enclosure 100. Further, the system and method of the invention may comprise any number of particle sensors 413 for determining particle size, shape and count distribution of the particles in air 002 or on any surface within the enclosure. Still further, the system and method of the invention may utilize ultraviolet, visible, or infrared spectroscopy in the condensate collection reservoir areas to provide information regarding the presence, and chemical characteristics, of the particles and pathogens removed from air 002.

Figure 14:
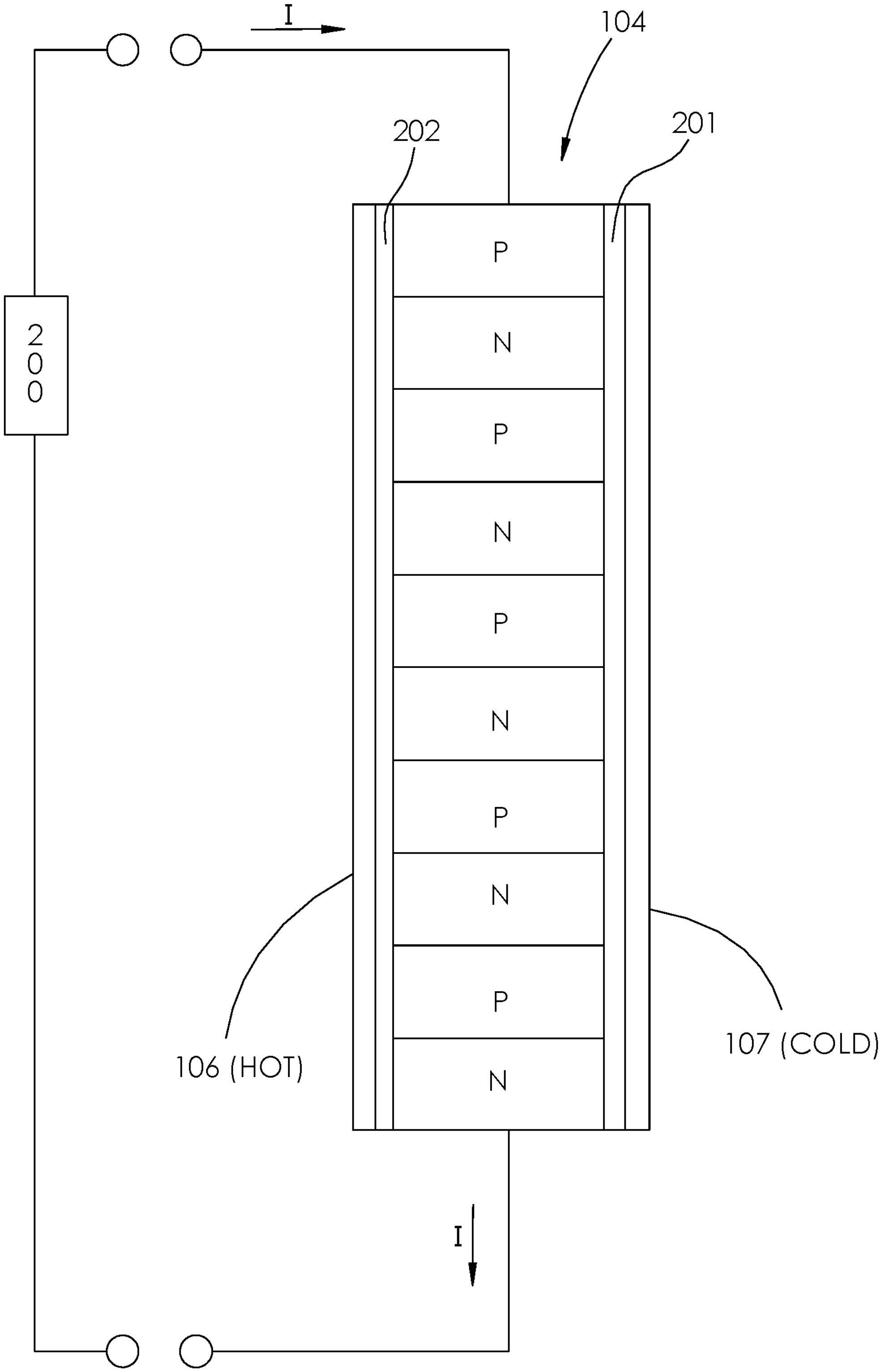
FIG. 14 depicts an exemplary, non-limiting embodiment of a thermoelectric module of the invention.

Referring now to FIG. 14, an exemplary embodiment of a thermoelectric module is depicted. An electric current I is supplied by current source 200, which may be an electric power supply. In this exemplary embodiment of thermoelectric module 104, a series of alternating semiconductor P and N sections, wherein the P and N materials have differing electron densities, may be sandwiched between thermally conductive plates 202 and 201. The successive semiconductor P-N junctions are connected electrically in series, but thermally in parallel, such that electric current I passes through the semiconductor P-N junctions causing a temperature differential to develop across surfaces 106 (hot surface) and 107 (cold surface). The Peltier effect produces a temperature flux resulting in a temperature differential between surfaces 106 (hot) and 107 (cold). In embodiments, as a non-limiting example, hot surface 106 may be held at any temperature up to and surpassing 56° C., and cold surface 107 may be held at any temperature down to, and below, 0° C. In embodiments, the temperature of any hot surface 106 may be between 20° C. and 100° C., inclusive. In embodiments, the temperature of any cold surface 107 may be between 20° C. down to 0° C., inclusive. Alternatively, in embodiments, the temperature of any hot surface 106 and any cold surface 107 may be in a range between 0° C. and 100° C., inclusive, wherein the hot surface 106 of a thermoelectric module 104 is at a higher temperature than cold surface 107 of that same thermoelectric module. The temperature of hot surface 106 and cold surface 107 may be adjusted by the physical configuration of thermoelectric module 104 and by control of the electric current I through thermoelectric module 104, for example, by the controllable power supply 401 as controlled by controller 402 depicted in FIG. 17, to achieve any desired temperature differential, or any desired temperature at hot surface 106 or cold surface 107, or both. Thermal electric module 104 may comprise other configurations that may comprise, instead of, or in combination with, P-N junctions, junctions of any materials that exhibit differing electron density, such as junctions of metals or other conductive materials. It is not necessary that thermoelectric modules 104 comprise semiconductor materials having P-N junctions as depicted in FIG. 14. The structure depicted in FIG. 14, is merely an exemplary embodiment of a Peltier-effect producing thermoelectric module of the invention 104. The scope of the invention is intended to include, but not be limited to, any structure of thermoelectric module 104 that exhibits the Peltier effect, resulting in a desired temperature differential between surfaces 106 and 107. This desired temperature differential, may be application-specific and may be any desired differential, for example only, in a range of 50° C. to 60° C., or, alternatively, in a range of 0° C. to 100° C. In embodiments the temperature differential may be, as an example, any desired temperature differential that produces condensation of the water in air 002 as it passes along and is in thermal communication with cold surface 107 in any given application of the system and method of the invention. It is understood that differing applications in, for example, differing environments or differing unwanted particle or pathogen loads, may experience incoming air 002 at differing relative and absolute humidity, different temperature, and containing different unwanted particulate or pathogen load. Since one object of the thermoelectric module 104 is to condense water from air 002, resulting in condensate 109 containing unwanted particles and pathogens, the desired temperature differential, and the desired temperatures between surfaces 106 and 107, may differ between specific applications, in differing environments, so as to manage power consumption of the system of the invention, produce a desired amount of condensate, and so on.

Still referring to FIG. 14, it is also to be understood that one object of the invention is to maintain a temperature differential between surfaces 106 and 107 so that the desired condensation of water from gas 002 is achieved, and that at this temperature differential may be achieved in any number of ways and by any number of means known for controlling the temperature of a surface. Thus, the scope of the invention is not limited to the use of Peltier modules, or to thermoelectric modules 104 that operate using the Peltier effect. Thermoelectric modules 104, and in fact any of the cold surfaces 107 or hot surfaces 106, may comprise any structure that is operable to produce a desired temperature differential between surfaces 106 and 107, or to produce specific temperatures as may be desired on surfaces 106 and 107. For example, and not by way of limitation, electrically resistive heating elements, circulation of hot fluids or cold fluids through heat exchangers, or any other means known in the art may be used to produce the desired temperatures on cold surfaces 107 or hot surfaces 106.

Still referring to FIG. 14, in embodiments, the hot surfaces 106 of thermoelectric modules 104 may be at or above 56° C. In embodiments, the temperature of hot surfaces 106 of thermoelectric modules 104 may be such it that causes evaporation of the water in condensate 109 as it comes into contact with hot surfaces 106, without boiling the water in condensate 109, in order to prevent ejecting the unwanted particles or pathogens back in to air 002.

Still referring to FIG. 14, in embodiments, the cold surfaces 107 may have a hydrophobic coating that allows the condensate 109 to quickly flow down and drip into to a collection reservoir 108 (see FIG. 1). The collection area may be coated with a contagion destroying catalyst(s) and may be heated to provide additional control over the evaporation and condensation balance. The thermoelectric module cold surfaces 107 may, in embodiments, be maintained at a temperature just above 0° C., however the cold surfaces may be maintained any temperature that is colder than the temperature of the incoming gas 002 to be cleaned in order to achieve a desired rate of condensation.

Still referring to FIG. 14, in embodiments, the hot surfaces 106 may comprise catalysts, such as copper or silver material, that neutralize pathogens. The increased temperature of surfaces 106 operates to increase the activity of the catalyst, reducing the time required for pathogen neutralization.

Still referring to FIG. 14, the surfaces of collection reservoirs 108 that come into contact with condensate 109 may be treated with, and comprise, a catalyst that neutralizes pathogens; and, further the surfaces of collection reservoirs 108 that come into contact with condensate 109 may be heated to increase the activity of the applied catalysts, resulting in a reduction in time to neutralize a given amount of a pathogen.

Figure 15:
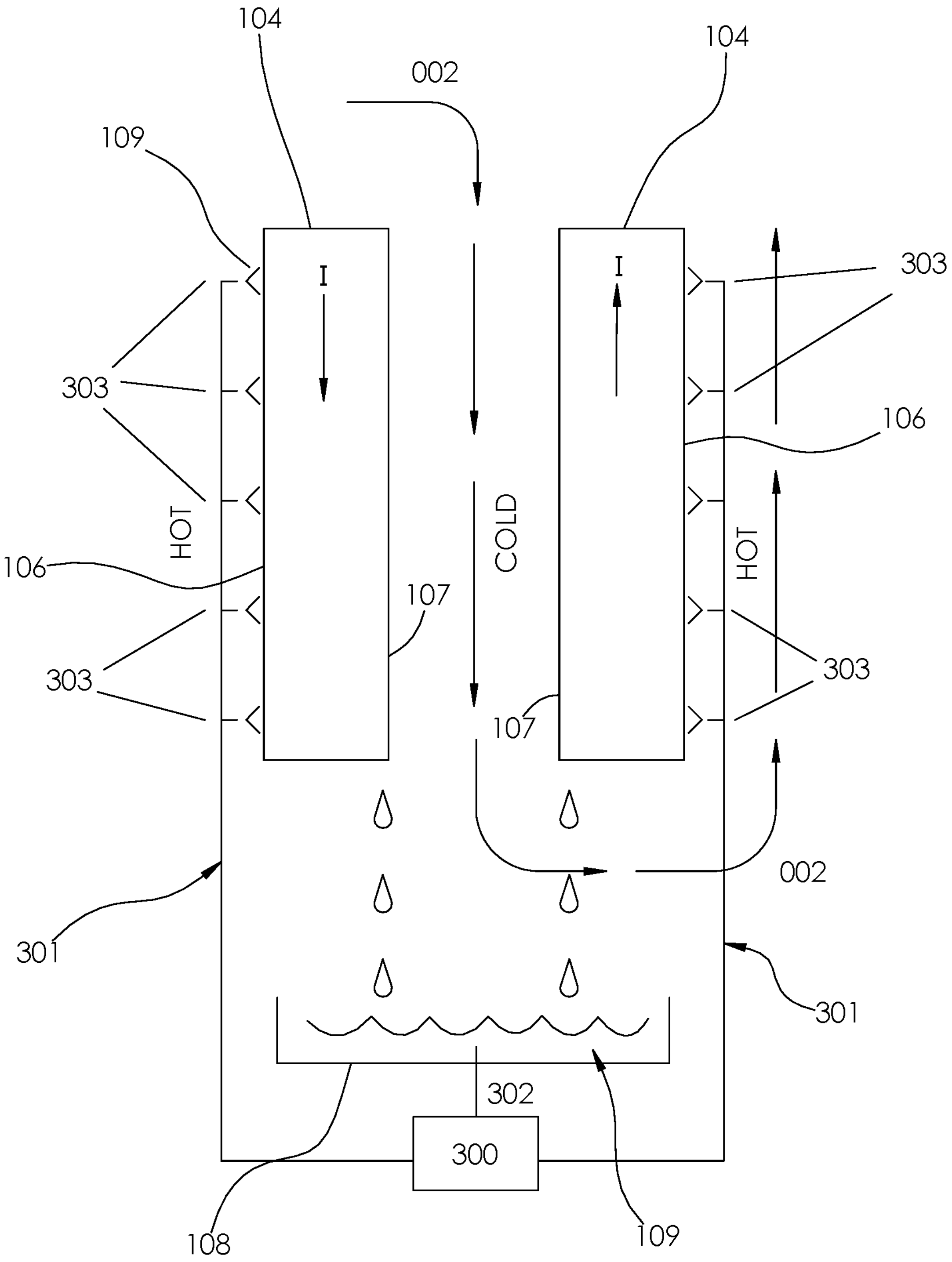
FIG. 15 depicts an exemplary, non-limiting embodiment of a thermoelectric module pair of the invention, depicting a condensation-collection-evaporation cycle of the invention, and depicting a spraying method of applying condensate 109 to hot surfaces 106.
Figure 16:
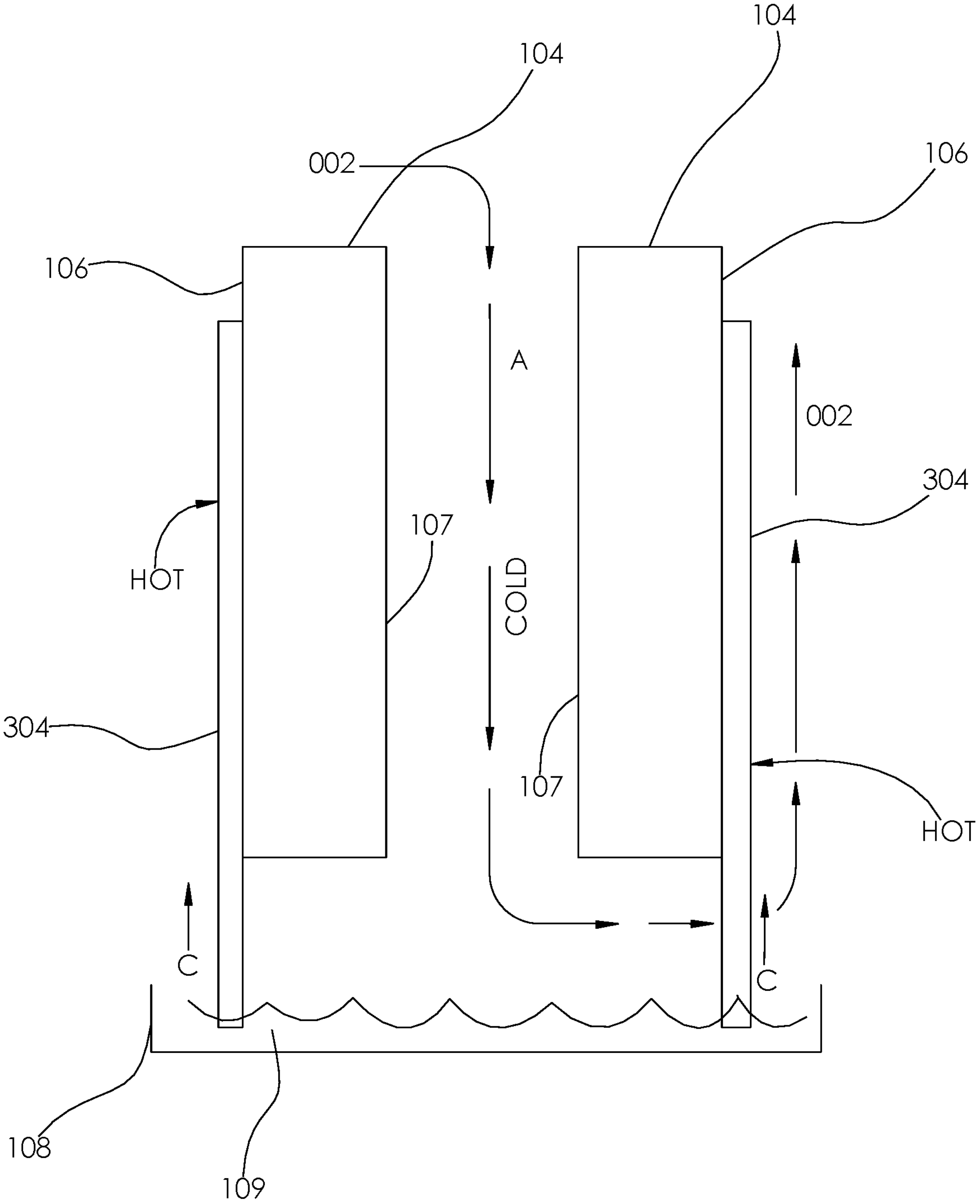
FIG. 16 depicts an exemplary, non-limiting embodiment of a thermoelectric module pair of the invention, depicting a condensation-collection-evaporation cycle of the invention, and depicting a wicking method of applying condensate 109 to hot surfaces 106.

Referring now to FIGS. 15 and 16, two alternative systems and methods for motivating condensate 109 on to thermoelectric modules 104 hot surfaces 106 are depicted and described below. The system and method of the invention may comprise any set of elements for communication condensate 109 onto the hot surfaces 106 of thermoelectric modules 104. Two non-limiting exemplary embodiments of such elements are described in FIGS. 3 and 4.

Referring now to FIG. 15, in an embodiment, an embodiment of a thermoelectric module pair of the invention is depicted. A pump 300, such as, for example, a micropump, which may be in fluid communication with collection reservoir 108 through, for example, tubing or other fluid communication means 302, or alternatively, is immersed in the condensate 109 in collection reservoir 108, may be controlled by a controllable power supply 401 to pump condensate 109 from the collection reservoir 108 through tubing or other fluid passageways 301 to micro-spray nozzles 303 which direct micro-sprayed condensate 109 onto the hot surfaces 106 of thermoelectric modules 104. The micro-spray elements 303 may incorporate ionization to improve the probability of the condensate spray interaction with the hot surfaces 106. The hot surfaces 106 may be coated with a catalyst material or combination of catalyst materials that effectively neutralize the contagion(s). In embodiments, the thermoelectric module hot surfaces 106 may be maintained at or above 56° C. The heat increases the activity of the catalyst and reduces the time for contagion neutralization. The heat may be adjusted by controller 402 through controllable power supply 401 for controlling current I to the thermoelectric modules 104 so that the hot surfaces 106 of the thermoelectric modules 104 evaporates the sprayed condensate 109 without boiling it, so as to not eject the removed pathogens or unwanted material such as particles or pathogens back into gas 002 (which may be air). Cold surfaces 107 of thermoelectric modules 104 are depicted for reference.

Referring now to FIG. 16, in an embodiment, condensate 109 may be also motivated from collection reservoir 108 onto thermoelectric modules 104 hot surfaces 106 using capillary, or wicking, action, for example and not by way of limitation, such as employed in heat pipes for microelectronics cooling. Such capillary or wicking structures may include, for example, micro-grooved copper tubing or sintered copper, for example sintered copper powder, having a porosity that allows wicking of a fluid through the wicking structure. Capillary structures 304 may be in contact with condensate 109 that is contained in collection reservoir 108 on a first end, and may wick condensate 109 in the direction of arrow C onto hot surface 106 of thermoelectric module 104, where the water forming condensate 109 is evaporated from hot surface 106 as herein described, leaving unwanted particles and pathogens on hot surface(s) 106. The wicking structure may be in physical contact or in thermal communication, or both, with hot surfaces 106. Cold surfaces 107 of thermoelectric modules 104 are depicted for reference.

The system and method of the invention may comprise any number of optional UVA, B or C light sources for the purpose of neutralizing pathogens by irradiating them with a total dose of light energy, or with a high enough power density rate, that the pathogens are neutralized. In embodiments, the UVA, B or C light source(s) are sources that do not produce ozone. The UVC light source may be in communication with a controllable power supply 401 for controlling electric power supplying the UVA, B or C light.

In embodiments, one or more level sensors that communicate information about a fluid level by producing an output signal, either analog or digital, proportional to a fluid level in a reservoir or other collection area may be used to sense the levels of water/solution, or fluid, in the collection areas. This level information may be used to adjust the temperature balance of the stages to prevent any overflow of water due to excess condensation, or the opposite condition of drying out of the collection area. In extremely dry ambient conditions water may need to be added periodically. Further, in embodiment, the invention may comprise ambient temperature sensors, and/or humidity sensors, in communication with controller 402.

In embodiments, particle sensors may be used in one or more of the collection areas to characterize the size, shape and count distribution of the particles. In further embodiments, spectroscopy may be used in one or more of the water collection areas to provide data on the presence and chemical characteristics of the contagions/contaminants removed from the air flow.

The combining of effects of several methods enables the system and method of the invention to be characterized by lower power consumption than equivalent HEPA and other systems while having high efficacy for pathogen removal, neutralization, and destruction.

Figure 17:
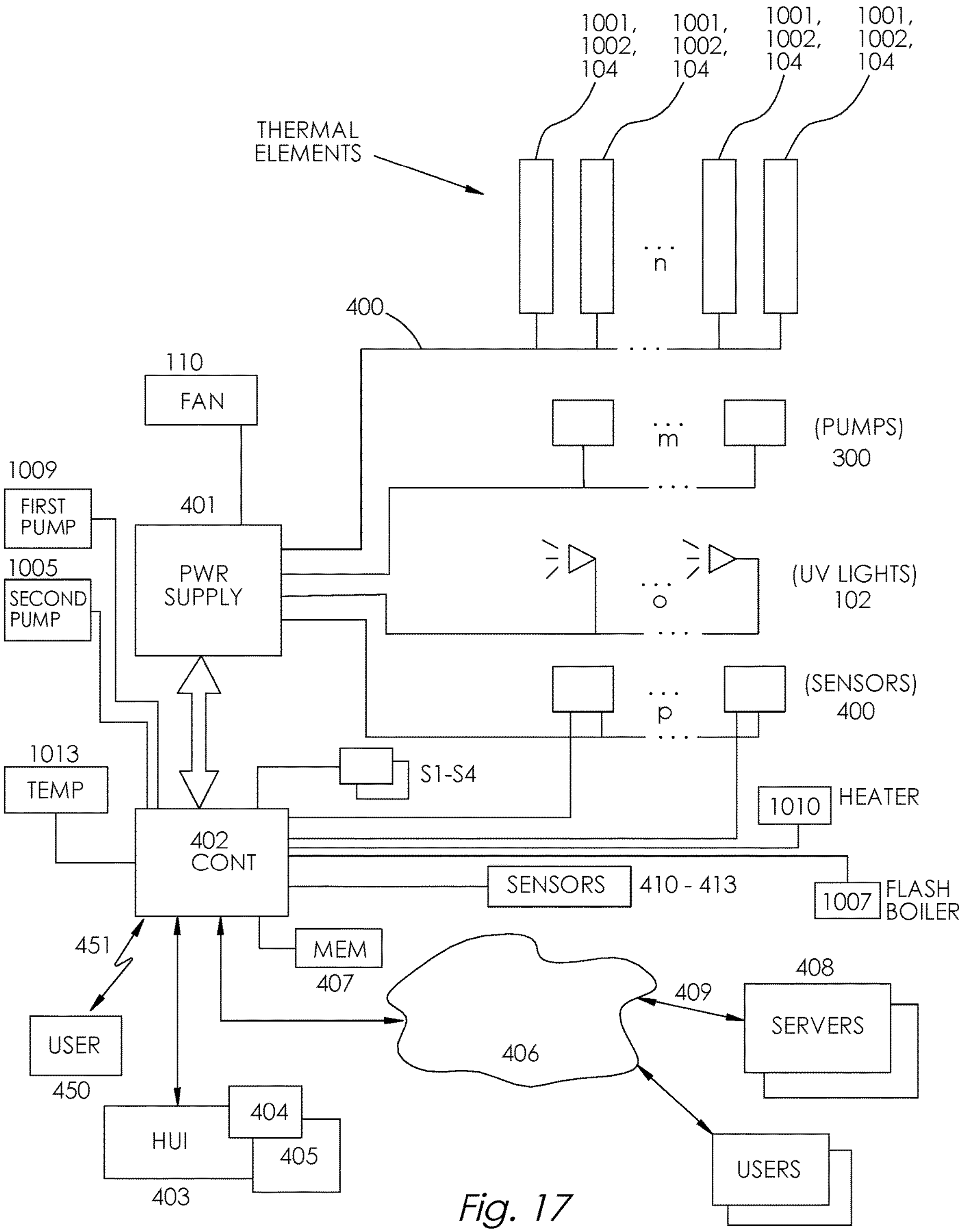
FIG. 17 depicts an exemplary, non-limiting block diagram of an embodiment of the invention.

Referring now to FIG. 17, a block diagram of an exemplary embodiment of the system of the invention is depicted. The system and method of the invention may comprise one or more fans or blowers for motivating air 002 through enclosure 100, temperature sensors, thermoelectric generators, fluid level sensors, power supplies, a computer and other electrically powered components in communication with one another as described herein and as depicted in the figures, and all legal equivalents.

Still referring to FIG. 17, the system and method of the invention may comprise a controller or processor 402. Processor or controller 402 may be in communication with a controllable power supply 401 for controlling power to the various elements of the system; with sensors 400 and 410-413 so as to be able to receive information from the sensors regarding physical parameter as described herein; and with a physical media storage (which may be semiconductor or other memory) element or elements 407 of any type known in the art such as, for example, solid state memory, non-volatile memory, magnetic media, optical media or other memory devices capable of storing, retrieving, and communicating information. Non-transitory computer readable and executable instructions may reside and be stored in the physical memory element 407 such that they can be read and executed by processor 402 for carrying out the steps of the method of the invention as described herein, and for carrying out the described features and elements of the invention. Processor 402 may also be in communication with a Human User Interface ("HUI") 403 that is operable to receive input from a user from any know human interface device including but not limited to keyboard, touchscreen, audio commands 404 or other human-computer interface modalities as are known in the art. HUI 403 may further comprise any number or type of human interface output devices such as video monitors, touchscreens, speakers, discrete lights or other devices, collectively 405, that are operable to communicate information from processor 402 or its memory 407 to a human user.

Still referring to FIG. 17, controller or processor 402 may also comprise electronic circuitry for receiving input and information from, or providing information to, or both, a remote user using an electronic computing device, such as mobile device, computer, cell phone, smart phone, electronic tablet, or other device that is in communication with the controller through any communication means or system known in the art such as, for example, any wireless or wired interface 407, the internet 406, the world wide web 406, cellular data or other wireless or wired networks such Wide Area Networks, (WANs), Local Area Networks (LANs) or other wired or wireless interface(s) that are operable to provide data communication between controller or processor 402 and a remote computer, server, database or user interface for the purposes of communicating with, retrieving information from, and providing information and commands to controller or processor 402. In addition, controller or processor 402 may be in wired or wireless communication directly with a user through a direct connection, WAN, LAN or other communicate means or systems such that a user may communicate directly with processor 402 to provide information or commands to processor 402, receive information from processor 402, or to pass any information necessary for the operation or maintenance of the system and method of the invention between user 450 and processor 402.

Still referring to FIG. 17, the sensors of the invention may provide a wide array of information (data) on the system in real time and may be stored, or logged, by the controller in memory. Various levels of user data presentation may be generated by processor 402 and presented to a user through HUI 403/404/405 from simple PASS/FAIL, to processed numerical data, to full raw data. All sensor data may be recorded in memory 407 and time-stamped. Remote control of the system, and retrieval and interpretation of sensor information and other data generated by the system of the invention may be accomplished through the use of mobile devices running applications, or remote computers running software, that are in communication with the controller of the invention through any wired or wireless data interface, using any data network as described herein, and all legal equivalents thereof. In embodiments, the system of the invention be addressable by a computer, mobile device, server, controller or other electronic device for controlling the system or for retrieving status or sensor information. This may be done, for example, via a web portal that is accessible via the world wide web or other communication network.

Still referring to FIG. 17, controllable power supply 401 may be in communication with thermoelectric modules 104, or with the heating or cooling elements (such as thermoelectric coolers, coolant fluid circulating pumps, heated fluid circulating pumps, electric resistive heating elements, and any other devices for heating and cooling) that cool surfaces 107 or heat surfaces 106. Processor/controller 402 may be operable to control each of these heating or cooling elements. Processor/controller 402 may be operable to control current I to each thermoelectric module 104 individually, or in pairs such as pairs forming a thermoelectric module pair, or in any other grouping. Further, processor/controller 402 may be operable to control the temperature of any surface 106 or 107 by controlling the element that is heating or cooling these surfaces. For example processor/controller 402 may be operable to control the electric current through an electrically resistive heating element that is used to produce hot surfaces 106, or it may control the temperature and flow rate of a liquid circulating through heat exchangers for heating surfaces 106 or cooling surfaces 107, in any of the embodiments of the system and method of the invention. Thus a user 450 may control or command processor 402, by passing such commands to processor 402 through HUI 403, direct user interface 451, remote user interface which may be, for example, connected wirelessly or wired to the world wide web such that a remote user 450 may access and command processor 402, such that electric current I supplied to one or more thermoelectric modules 104 is controlled by processor 402 through controllable power supply 401; or to otherwise control the temperature of hot surfaces 106 or cold surfaces 107. Likewise, controllable power supply 401 may be in communication with the various pumps 300 of the invention such that they may be controlled as commanded by a user to be in ON state, an OFF state, or to pump at a determined flow rate. Also likewise, power supply 401 may be in communication with the various UVA, B or C or other ultraviolet ("UV") lights 102 of the system such that they may be controlled as commanded by a user to be in ON state, an OFF state, or to radiate UVA, B or C or UV energy at a determined intensity. Controllable power supply 401 may be used to control power to any or all system elements, such as the one or more fans or blowers 110. Thus, controller 402 is able to command the system of the invention into an operational state when commanded or when external or other sensor data indicates it should do so. Controller 402 is also able to command the system of the invention into a non-operational state in which no gas 002 is being motivated through the system of the invention. Controller 402 is thus able to control any temperature of cold surfaces 107, hot surfaces 106, flow rate of all pumps, temperature of condensate 109 in collection reservoir 108, rate of gas flow through the enclosure, and all other operating parameters of the system.

Figure 18:
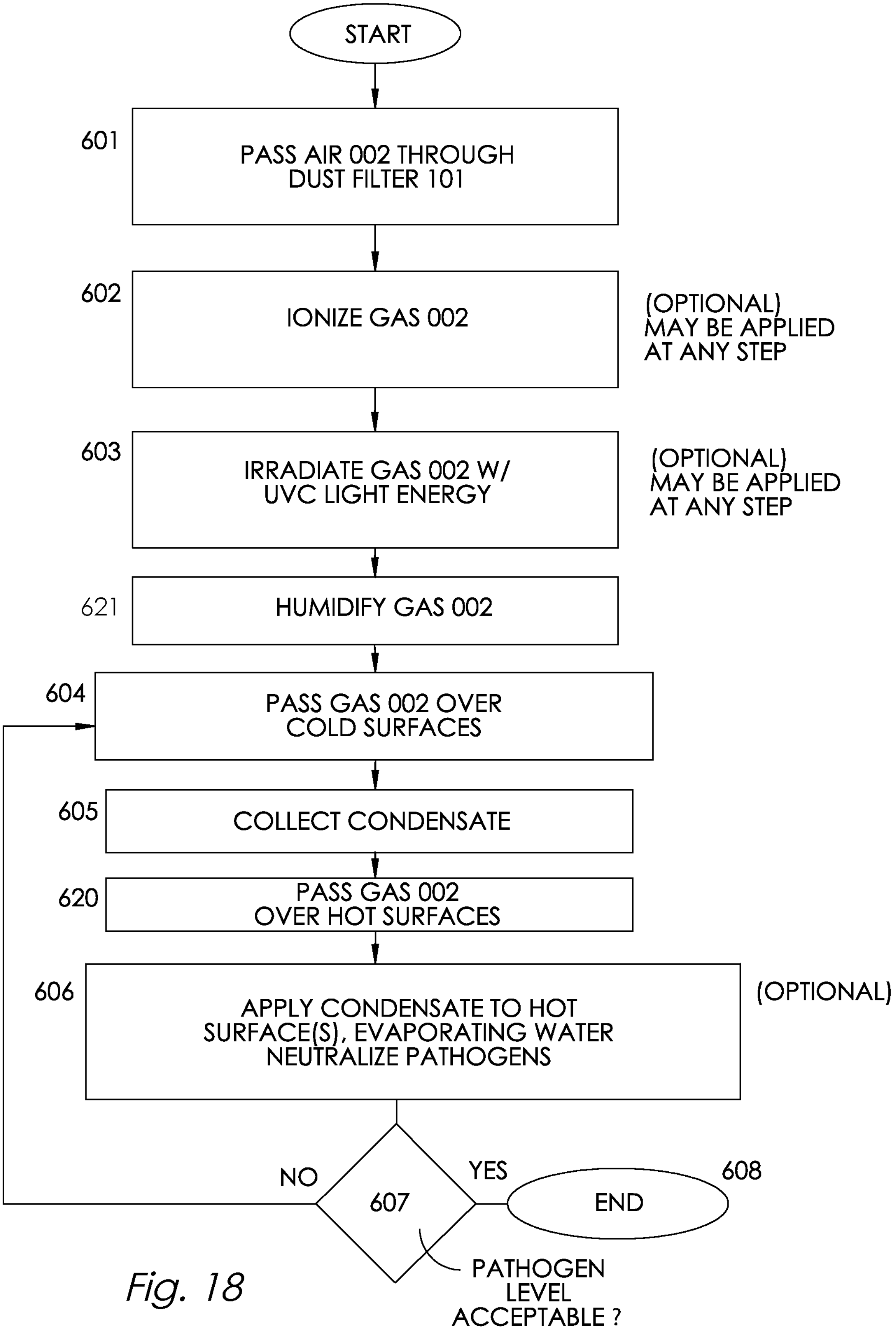
FIG. 18 depicts a flow chart of the method steps of an exemplary, non-limiting embodiment of the method of the invention.

Referring now to FIG. 18, an exemplary flow chart depicting an embodiment of the method of the invention is depicted. The flow of method steps depicted in FIG. 18 is exemplary in nature. It is to be understood that the scope of the invention is intended to include any combination or sequence of steps that include a cooling-collecting-neutralizing sequence of steps. In embodiments, the method of the invention may comprise the following steps, in any order.

In a first optional step 601, incoming gas to be cleaned 002 may enter enclosure 100, being motivated by, for example, one or more fans or blowers 110 or other equivalent means, or alternatively, incoming gas 002 may be motivated by external fans or blowers, such as when used to clean air in an HVAC ducting system. Gas 002, which may be air, may optionally be passed through a dust filter 101 to remove larger particles from the air, such as dust or pollen particles from air 002 in order to keep the elements of the system from becoming fouled by a collection of dust and other particles.

In an optional step 602, the incoming gas 002 may be ionized using any ionization technique or devices as described herein. For example, an electrically charged ionizing grid may be used to ionize incoming gas 002, and the unwanted materials being carried in gas 002, or both, as gas 002 passes through the grid. In embodiments, the ionization step may be carried out by one or more high voltage probes, wires subjected to an electric voltage or current, nanotextured surfaces or other ionization means 103 as may be known in the art.

In an optional step 603, air 002 may be irradiated by any source or multiple sources of UVA, B or C light energy to begin the process of neutralizing pathogens in gas 002. Step 603 may occur in one or more iterations, and at any point, in the system and method of the invention.

In step 621, gas 002 may be humidified by water droplets, micro droplets, or mist. This addition of water to gas 002 provides a greater volume of water for condensation has gas 002 comes into thermal contact with cold surface(s) 107, removing more unwanted material from the air. In dry environments, or where incoming gas 002 is at a very low relative humidity, misting (for example, using mister or ultrasonic nebulizer 120) may be desirable in order for the system of the invention to remove a desired amount of unwanted material from gas 002.

In steps 604 and 605, the gas 002 is passed over a first cold surface 107 of the invention such that gas 002 is in thermal communication with a cold surface 107, which may be for example passing air 002 between two opposing cold surfaces 107 of a pair of thermoelectric modules forming a thermoelectric module pair, causing water in gas 002 to condense and to be collected as condensate 109 in a collection reservoir 108. The invention may comprise any number of cold surfaces 107, which all do not necessarily need to be held at the same temperature or within the same temperature range, but, in embodiments, the cold surfaces of the invention may be held at the same temperature or within the same temperature range. In an embodiment the cold surfaces of the invention may be held at any temperature, as an example, in a range of 0° C. to +10° C. As a further example the cold surfaces of the invention 107 may be held at or near 0° C. The condensate 109 will contain unwanted particulates and pathogens, including viruses that may be airborne, such as the virus that causes Covid-19 disease, that have been removed from gas 002. Any of the cold surfaces 107 comprising the invention may be coated with a hydrophobic coating enabling the condensate to run quickly and efficiently off the cold surfaces into a collection reservoir.

In step 620, gas 002 that has been cooled may be motivated to come into thermal communication with hot surface(s) 106, heating gas 002 such that it is able to absorb, or carry a greater amount of water and thus enabling a higher volume of condensate to form in a subsequent cooling stage, removing a greater amount of unwanted material from gas 002. Hot surfaces 106 may also be useful for heating gas 002 before it exits as cleaned gas 002 in order to provide thermal balance to the system and to return the cleaned gas 003 to the environment outside enclosure 100 at a desired temperature. In other words, it may be desired that outlet gas 003 be at, above, or below room temperature, which is controllable by controller 402 controlling the temperature of one or more hot surfaces 106.

In embodiments of the method, in step 606, condensate 109 may be communicated to a hot surface 106, or a plurality of hot surfaces, which may be the hot surface(s) 106 of one or more thermoelectric modules 104, causing heat energy to be transferred to water in the condensate, evaporating the water of the condensate, but preferably not boiling the condensate 109, and leaving the unwanted particles and pathogens adhered to the hot surface 106. In embodiments the hot surface 106 may comprise a catalytic material, or coating, having pathogen-neutralizing properties such as anti-bacterial or anti-viral properties for the purpose of neutralizing pathogens. Such coatings may comprise copper or silver mixtures or other catalytic materials as described herein and all their legal equivalents. In embodiments, as a non-limiting example, hot surface 106 may be held at any temperature up to and surpassing 56° C., and cold surface 107 may be held at any temperature down to, and below, 0° C. In embodiments, the temperature of any hot surface 106 may be between 20° C. and 100° C., inclusive. In embodiments, the temperature of any cold surface 107 may be between 20° C. down to 0° C., inclusive. Alternatively, in embodiments, the temperature of any hot surface 106 and any cold surface 107 may be in a range between 0° C. and 100° C., inclusive, wherein the hot surface 106 of a thermoelectric module 104 is at a higher temperature than cold surface 107 of that same thermoelectric module. The temperature of hot surface 106 and cold surface 107 may be adjusted by the physical configuration of thermoelectric module 104 and by control of the electric current I through thermoelectric module 104, for example, by the controllable power supply 401 as controlled by controller 402 depicted in FIG. 5, to achieve any desired temperature differential, or any desired temperature at hot surface 106 or cold surface 107, or both.

In step 607, the level of unwanted material in outlet gas 003 may be measured by sensors 400, which are in communication with controller 402 (see FIG. 17). If the level of unwanted material in outlet gas 003 is acceptable, the system may be controlled into a non-operational state by controller 402. If the level of unwanted material in exit gas 003 is not acceptable, the system and method may continue to operate until the level of unwanted material in gas 002 is acceptable.

In a final step, the unwanted particles and neutralized pathogens may be removed from the hot surface(s) of the invention. This waste does not represent a biohazard, as any pathogens have been neutralized by the system and method of the invention, i.e. they are no longer operable or viable.

Figure 19:
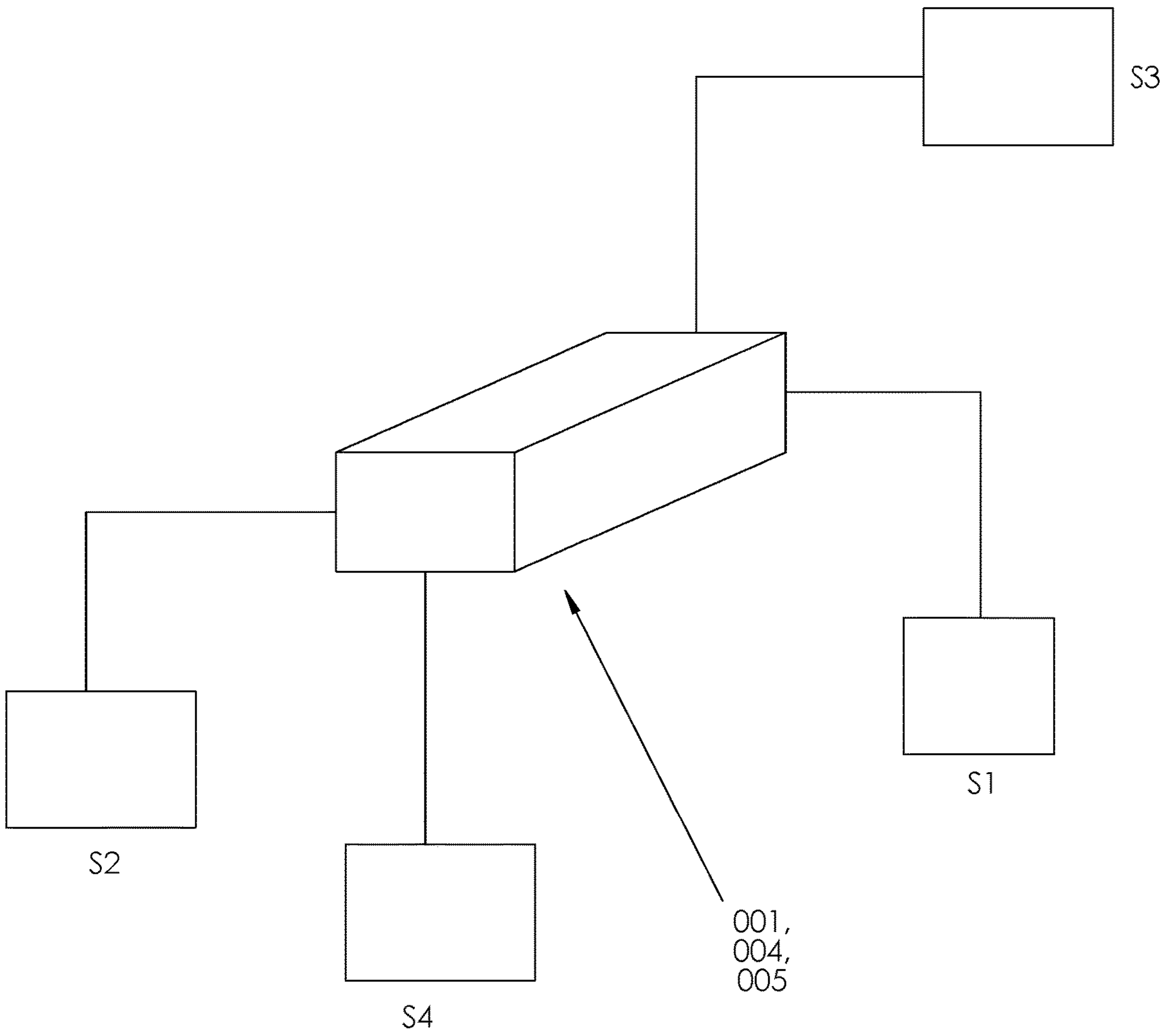
FIG. 19 depicts an embodiment of the system in which external pathogen or particle sensor are in communication with controller 402, such that when unwanted material such as pathogens or particles are detected in the environment outside the system 001, 004 or 005 of the invention, such as in an enclosed area, room, building, air duct or other structure, controller 402 may cause the system and method of the invention to operate for the purpose of removing the unwanted material from the local environmental air. It is not necessary that the sensors be local to the system.

Referring now to FIG. 19, an embodiment of the invention comprising external pathogen or particle sensors S1-S4 is depicted. In this embodiment of the system, external pathogen or particle sensors are in communication with controller 402, such that when unwanted material such as pathogens or particles are detected in the environment outside the enclosure 100 of the invention, such as in an enclosed area, room, building, air duct or other structure, controller 402 may cause the system and method of the invention to operate, motivating air through the enclosure such that it comes into thermal communication with cold surface(s) 107, resulting in the formation of condensate 109 as hereinbefore described, for the purpose of removing the unwanted material from the local environmental air. It is not necessary that sensors S1-S4 be local to the system. While four sensors S1-S4 are depicted in FIG. 19, any number of external sensors may comprise the invention, and they may be located in any desired location. Sensors S1-S4 may be in wired or wireless communication with controller 402. In embodiments, controller 402 may be adapted to receive sensor information from one or more external sensors S1-S4, and to control the system of the invention into an operational state when one or more sensors detect that an unwanted material is present in the environment outside an enclosure of the system. "Operational state" means that system of the invention is receiving inlet gas 002, causing the inlet gas 002 to be motivated through enclosure 100, causing gas 002 to come into contact with cold surface(s) 107 and hot surface(s) 106, forming condensate 109 that removed unwanted materials from gas 002, and exiting the cleaned gas 003 from the enclosure as described herein.

In any of the embodiments of the system and method of the invention, the invention may comprise any number or combination of baffles, plenums, pathways, fans, blowers or other structures and devices known in the art for motivating and directing the flow of gas 002 within enclosure 100 such that gas 002 is motivated and directed as described herein.

In any of the embodiments of the system and method of the invention, the at least one cold surface(s) 107 may comprises a hydrophobic coating. In any of the embodiments of the system and method of the invention, the at least one hot surface(s) 106 may comprise a catalytic material for neutralizing a pathogen.

In any of the embodiments, the source of motivation of the continuing volume of gas (which may be, for example, air) through the enclosure of the invention may be external. For example, in an embodiment in which the continuing volume of gas is the air moving through an HVAC system, such as when an enclosure of the invention receives a continuing volume of air at the inlet 2013, the incoming air may already be motivated by fans or blowers of the HVAC system. In this case, the continuing volume of gas may be motivated through the enclosure by the HVAC fans or blowers. In such cases, it may not be necessary that fans, blowers or other gas motivating means comprise the invention.

In any of the embodiments, as a non-limiting example, hot surface 106 may be held at any temperature up to and surpassing 56° C., and cold surface 107 may be held at any temperature down to, and below, 0° C. In embodiments, the temperature of any hot surface 106 may be between 20° C. and 100° C., inclusive. In embodiments, the temperature of any cold surface 107 may be between 20° C. down to 0° C., inclusive.

A prototypical, single-stage (i.e. that contained only one cold surface and one hot surface) embodiment of the invention was built and tested in a laboratory environment. The gas 002 to be cleaned was air. The system achieved an air flow rate of 200 cubic feet per minute. For test purposes, the unwanted material injected into air 002 was MS-2 bacteriophage (ATCC 15597-B1) aerosol. Testing was performed in a 945 cubic foot test chamber. The MS-2 bacteriophage was harvested and titrated to 8E8 pfu/ml. A suspension of the organism was then aerosolized into the test chamber using a nebulizer prior to powering the test device. The test chamber air was sampled at 15-minute intervals using a SKC Bio-Stage cascade impactor for 1-minute sampling periods. The cascade impactors were calibrated to an airflow rate of 28.3 liters/min and the sampling inlet was situated at the midpoint of the test chambers. The recovered organisms were enumerated after 24-72 hours of incubation. The test conditions were 72° F. and fifty percent (50%) relative humidity. The air cleaned by the test device was compared to chamber (i.e., uncleaned) air at 15, 30, 45 and 60 minutes after powering the test device, with the following results: 1) at 15 minutes, 13.85% of the unwanted material had been removed from air 002 by the system; 2) at 30 minutes, 50.31% of the unwanted material had been removed from air 002 by the system; 3) at 45 minutes, 89.43% of the unwanted material had been removed from air 002 by the system; and 4) at 60 minutes, 97.6% of the unwanted material had been removed from air 002 by the system.

The various embodiments of the invention may be comprised of the individual elements, limitations and method steps of the invention shown and described herein, including their legal equivalents, in any number, in any combination, and in any order.

What is claimed is:

1. A system for removing unwanted materials from a continuing volume of gas, comprising:

an enclosure comprising a fan for moving a continuing volume of gas through the enclosure, the enclosure having an inlet enabling the continuing volume of air to enter the enclosure, and a second opening enabling the continuing volume of gas to exit the enclosure, the continuing volume of gas characterized by a temperature;

at least one cold surface that is at a lower temperature than the continuing volume of gas, such that water in the air condenses and precipitates from the gas as the gas comes into thermal communication with the at least one cold surface, forming a condensate comprising the unwanted materials;

at least one hot surface that is at a higher temperature than the continuing volume of gas, that heats the continuing volume of gas as the gas comes into thermal communication with the at least one hot surface; and at least one collection reservoir in fluid communication with the condensate so that it collects the condensate;

wherein the continuing volume of gas is motivated though an outlet opening, wherein the continuing volume of gas that exits the enclosure through the outlet opening has a lower count of unwanted materials to volume of gas than the continuing volume of gas that entered the enclosure;

further comprising at least one mister in communication with a source of fluid, for increasing the volume of water carried by the continuing volume of gas;

wherein said source of fluid is a flash boiler that is in communication with the at least one collection reservoir, such that condensate from said at least one collection reservoir is communicated to the flash boiler, where the condensate is heated such that pathogens in the condensate are neutralized, and wherein the resulting heated condensate is communicated to the mister for increasing the amount of water in the continuing volume of gas.

2. A system for removing unwanted materials from a continuing volume of gas, comprising:

an enclosure comprising a fan for moving a continuing volume of gas through the enclosure, the enclosure having an inlet enabling the continuing volume of air to enter the enclosure, and a second opening enabling the continuing volume of gas to exit the enclosure, the continuing volume of gas characterized by a temperature;

at least one cold surface that is at a lower temperature than the continuing volume of gas, such that water in the air condenses and precipitates from the gas as the gas comes into thermal communication with the at least one cold surface, forming a condensate comprising the unwanted materials;

at least one hot surface that is at a higher temperature than the continuing volume of gas, that heats the continuing volume of gas as the gas comes into thermal communication with the at least one hot surface; and at least one collection reservoir in fluid communication with the condensate so that it collects the condensate;

and wherein the continuing volume of gas is motivated though an outlet opening, wherein the continuing volume of gas that exits the enclosure through the outlet opening has a lower count of unwanted materials to volume of gas than the continuing volume of gas that entered the enclosure;

wherein said enclosure comprises a plurality of stackable stages, including at least one inlet stage and at least one outlet stage, wherein the inlet stage receives a continuing volume of gas, passes the continuing volume of gas in proximity to a plurality of alternating cold and hot surfaces, and exits the continuing volume of gas into a following stage, which may be a first intermediate stage of an intermediate stage pair or an outlet stage; and wherein:

in the case in which the following stage is a first intermediate stage of an intermediate stage pair, wherein, in the intermediate stage pair, the continuing volume of gas passes through the intermediate stage pair, coming into thermal communication with a plurality of alternating cold and hot surfaces, resulting in the formation of condensate when the gas comes into thermal communication with the cold surfaces of the intermediate stage pair, and wherein the continuing volume of gas exits into a following stage, which may be another first intermediate stage of an intermediate stage pair, or an outlet stage; and in the case in which the following stage is an outlet stage, in the outlet stage, the continuing volume of gas passes through the outlet stage, coming into thermal communication with a plurality of alternating cold and hot surfaces, resulting in the formation of condensate when the gas comes into thermal communication with the cold surfaces of the outlet stage, and wherein the continuing volume of gas exit the enclosure through an outlet opening in the outlet stage.

3. The system of claim 2, wherein the system comprises an inlet stage, and an outlet stage.

4. The system of claim 2, wherein the system comprises an inlet stage, an intermediate stage pair, and an outlet stage.

5. The system of claim 2, wherein the system comprises an inlet stage, a plurality of intermediate stage pairs, and an outlet stage.

6. A system for removing unwanted materials from a continuing volume of gas, comprising:

an enclosure comprising a fan for moving a continuing volume of gas through the enclosure, the enclosure having an inlet enabling the continuing volume of air to enter the enclosure, and a second opening enabling the continuing volume of gas to exit the enclosure, the continuing volume of gas characterized by a temperature;

at least one cold surface that is at a lower temperature than the continuing volume of gas, such that water in the air condenses and precipitates from the gas as the gas comes into thermal communication with the at least one cold surface, forming a condensate comprising the unwanted materials;

at least one hot surface that is at a higher temperature than the continuing volume of gas, that heats the continuing volume of gas as the gas comes into thermal communication with the at least one hot surface; and at least one collection reservoir in fluid communication with the condensate so that it collects the condensate;

wherein the continuing volume of gas is motivated though an outlet opening, wherein the continuing volume of gas that exits the enclosure through the outlet opening has a lower count of unwanted materials to volume of gas than the continuing volume of gas that entered the enclosure;

wherein the at least one cold surface is a cold surface of a thermoelectric module, and wherein the at least one hot surfaces is a hot surface of a thermoelectric module; and wherein said continuing volume of gas is directed to pass between the cold surfaces of a pair of thermoelectric modules arranged so that their cold surfaces are opposing, forming an open volume between them, through which said air passes causing said air to come into thermal communication with said cold surfaces such that the temperature of said air is lowered, forming condensate.

7. A system for removing unwanted materials from a continuing volume of gas, comprising:

an enclosure comprising a fan for moving a continuing volume of gas through the enclosure, the enclosure having an inlet enabling the continuing volume of air to enter the enclosure, and a second opening enabling the continuing volume of gas to exit the enclosure, the continuing volume of gas characterized by a temperature;

at least one cold surface that is at a lower temperature than the continuing volume of gas, such that water in the air condenses and precipitates from the gas as the gas comes into thermal communication with the at least one cold surface, forming a condensate comprising the unwanted materials;

at least one hot surface that is at a higher temperature than the continuing volume of gas, that heats the continuing volume of gas as the gas comes into thermal communication with the at least one hot surface; and at least one collection reservoir in fluid communication with the condensate so that it collects the condensate;

wherein the continuing volume of gas is motivated though an outlet opening, wherein the continuing volume of gas that exits the enclosure through the outlet opening has a lower count of unwanted materials to volume of gas than the continuing volume of gas that entered the enclosure;

wherein the at least one cold surface is a cold surface of a thermoelectric module, and wherein the at least one hot surfaces is a hot surface of a thermoelectric module;

further comprising at least one mister in communication with a source of fluid, for increasing the volume of water carried by the continuing volume of gas;

wherein said source of fluid is a flash boiler that is in communication with the at least one collection reservoir, such that condensate from said at least one collection reservoir is communicated to the flash boiler, where the condensate is heated such that pathogens in the condensate are neutralized, and wherein the resulting heated condensate is communicated to the mister for increasing the amount of water in the continuing volume of gas.

8. A system for removing unwanted materials from a continuing volume of gas, comprising:

an enclosure comprising a fan for moving a continuing volume of gas through the enclosure, the enclosure having an inlet enabling the continuing volume of air to enter the enclosure, and a second opening enabling the continuing volume of gas to exit the enclosure, the continuing volume of gas characterized by a temperature;

at least one cold surface that is at a lower temperature than the continuing volume of gas, such that water in the air condenses and precipitates from the gas as the gas comes into thermal communication with the at least one cold surface, forming a condensate comprising the unwanted materials;

at least one hot surface that is at a higher temperature than the continuing volume of gas, that heats the continuing volume of gas as the gas comes into thermal communication with the at least one hot surface; and at least one collection reservoir in fluid communication with the condensate so that it collects the condensate;

wherein the continuing volume of gas is motivated though an outlet opening, wherein the continuing volume of gas that exits the enclosure through the outlet opening has a lower count of unwanted materials to volume of gas than the continuing volume of gas that entered the enclosure;

wherein the at least one cold surface is a cold surface of a thermoelectric module, and wherein the at least one hot surfaces is a hot surface of a thermoelectric module;

wherein said at least one thermoelectric module is defined as plurality of an even number of thermoelectric modules, wherein two thermoelectric modules form a thermoelectric module pair, wherein the thermoelectric modules comprising the thermoelectric module pair are arranged so that their cold surfaces are opposing one another, forming an open volume between them, through which said air passes, causing said air to come into contact with, or pass near, said cold surfaces such that the temperature of said air is reduced, causing condensate to form on said cold surfaces, said condensate containing unwanted particles or pathogens that have been removed from said air.

9. The system of claim 8, comprising a plurality of thermoelectric module pairs and a plurality of collection reservoirs, one collection reservoir for each thermoelectric module pair and each collection reservoir associated with a specific thermoelectric module pair, each of said collection reservoirs disposed so as to collect condensate that is motivated from said cold surfaces of the associated thermoelectric module pair by the force gravity.

10. The system of claim 9, wherein said cold surfaces comprise a hydrophobic coating.

11. The system of claim 9, wherein said hot surfaces comprise a catalytic material.

12. The system of claim 9, further comprising at least one pump in fluid communication with at least one of said collection reservoirs for pumping said condensate from said collection reservoirs, further comprising a spray or microspray nozzle in flow communication with said pump, wherein said pump is configured to pump said condensate from said collection reservoir and sprayed onto said hot surfaces through said spray or said microspray nozzle.

13. The system of claim 9, further comprising at least one wicking structure in fluid communication with at least one of said collection reservoirs for wicking said condensate from said collection reservoirs onto said at least one hot surface.

14. The system of claim 13 in which said wicking structure is microgrooved copper tubing.

15. The system of claim 13 in which said wicking structure is sintered copper.

16. A system for removing unwanted materials from a continuing volume of gas, comprising:

an enclosure comprising a fan for moving a continuing volume of gas through the enclosure, the enclosure having an inlet enabling the continuing volume of air to enter the enclosure, and a second opening enabling the continuing volume of gas to exit the enclosure, the continuing volume of gas characterized by a temperature;

at least one cold surface that is at a lower temperature than the continuing volume of gas, such that water in the air condenses and precipitates from the gas as the gas comes into thermal communication with the at least one cold surface, forming a condensate comprising the unwanted materials;

at least one hot surface that is at a higher temperature than the continuing volume of gas, that heats the continuing volume of gas as the gas comes into thermal communication with the at least one hot surface; and at least one collection reservoir in fluid communication with the condensate so that it collects the condensate;

and wherein the continuing volume of gas is motivated though an outlet opening, wherein the continuing volume of gas that exits the enclosure through the outlet opening has a lower count of unwanted materials to volume of gas than the continuing volume of gas that entered the enclosure, wherein:

at least one fan for motivating said air into, and through said enclosure, such that at least a portion of said air comes into thermal communication with said cold surfaces;

a controller operable to control said fan;

wherein said controller is in communication with a physical memory comprising non-transitory computer readable and executable instructions for controlling power to said fan and said thermoelectric modules;

and wherein said controller is adapted to receive user commands for controlling power to said fan and to said thermoelectric modules through at least one of a human user interface or a remote user in communication with said controller.

17. The system of claim 16 wherein controller is further adapted to receive sensor information from one or more external sensors, and, and to control the system of the invention into an operational state when one or more sensors detect that an unwanted material is present in the environment outside an enclosure of the system.

18. The system of claim 16 wherein controller is further adapted to receive sensor information from one or more internal sensors, and to communicate said sensor information to a user through said human user interface or to communicate said sensor information to a remote user in communication with said controller.

19. A method for removing unwanted particles and pathogens from a continuing volume of gas, comprising the steps of:

a. Cooling the continuing volume of gas such that water in the air condenses, forming a condensate containing the unwanted particles and pathogens that have been removed from the continuing volume of gas;

b. Collecting the condensate;

c. Applying the condensate to at least one hot surface, causing water forming the condensate to evaporate, leaving the unwanted particles and pathogens on the hot surface;

wherein said at least one hot surface is at a temperature in the range of 50° C. to 60° C., inclusive; and removing the unwanted particles and neutralized pathogens from the hot surface.

20. The method of claim 19, wherein the step of cooling the continuing volume of gas is performed by passing said continuing volume of gas between opposing cold surfaces of at least one thermoelectric module pair, wherein at least a portion of said continuing volume of gas is in thermal communication with at least one of said cold surfaces.

21. The method of claim 20, wherein said cold surfaces are at a temperature in a range between 0° C. and 10° C., inclusive.

* * * * *